(12) United States Patent
Holm et al.

(10) Patent No.: US 7,217,431 B2
(45) Date of Patent: May 15, 2007

(54) CONTROLLED AGGLOMERATION

(75) Inventors: Per Holm, Vanløse (DK); Anders Buur, Allerød (DK); Michiel Onne Elema, Copenhagen (DK); Birgitte Møllgaard, Virum (DK); Jannie Egeskov Holm, Valby (DK); Kirsten Schultz, Roskilde (DK)

(73) Assignee: LifeCycle Pharma A/S, Horsholm (DK)

( * ) Notice: Subject to any disclaimer, the term of this patent is extended or adjusted under 35 U.S.C. 154(b) by 0 days.

(21) Appl. No.: 10/482,558

(22) PCT Filed: Jul. 5, 2002

(86) PCT No.: PCT/DK02/00472

§ 371 (c)(1),
(2), (4) Date: Jul. 26, 2004

(87) PCT Pub. No.: WO03/004001

PCT Pub. Date: Jan. 16, 2003

(65) Prior Publication Data

US 2005/0008706 A1    Jan. 13, 2005

(30) Foreign Application Priority Data

Jul. 6, 2001    (DK)    .................. PA 2001 01071

(51) Int. Cl.
*A61K 9/19*    (2006.01)
*A61K 9/20*    (2006.01)

(52) U.S. Cl. .................. 424/474; 424/78.08; 424/458; 424/459; 424/461; 424/464; 424/470; 424/497; 428/357; 428/402; 428/403; 428/407

(58) Field of Classification Search ................ 428/357, 428/402, 403, 407; 424/78.08, 458, 459, 424/461, 464, 470, 474, 497
See application file for complete search history.

(56) References Cited

FOREIGN PATENT DOCUMENTS

| DE | 1 930 068 | 12/1970 |
| EP | 0 306 465 A1 | 3/1989 |
| JP | 59-40828 | 9/1985 |
| WO | WO 99/13864 | 3/1999 |
| WO | WO 01/22941 A1 | 4/2001 |

OTHER PUBLICATIONS

A. Faham et al., *Pharmazie*, 55(6):444-448 (2000).
Database WPI Week 8303 Derwent Publications Ltd., XP002217469 (1982).
Database WPI Week 8544 Derwent Publications Ltd., XP002180851 (1985).

*Primary Examiner*—Irina S. Zemel
(74) *Attorney, Agent, or Firm*—Peter F. Corless; Stephana E. Patton; Edwards Angell Palmer & Dodge LLP

(57) ABSTRACT

A process for the preparation of a particulate material by a controlled agglomeration method, i.e. a method that enables a controlled growth in particle size. The method is especially suitable for use in the preparation of pharmaceutical compositions containing a therapeutically and/or prophylactically active substance which has a relatively low aqueous solubility and/or which is subject to chemical decomposition. The process comprising i) spraying a first composition comprising a carrier, which has a melting point of about 5° C. or more which is present in the first composition in liquid form, on a second composition comprising a material in solid form, the second composition having a temperature of at the most a temperature corresponding to the melting point of the carrier and/or the carrier composition and ii) mixing or others means of mechanical working the second composition onto which the first composition is sprayed to obtain the particulate material.

44 Claims, 8 Drawing Sheets

CONTROLLED AGGLOMERATION

FIELD OF THE INVENTION

The present invention relates to a process for the preparation of a particulate material by a controlled agglomeration method, i.e. a method that enables a controlled growth in particle size. The method is especially suitable for use in the preparation of pharmaceutical compositions containing a therapeutically and/or prophylactically active substance which has a relatively low aqueous solubility and/or which is subject to chemical decomposition. By employment of the novel process, compositions can be prepared that have improved properties with respect to release of the active substance from the composition as evidenced by in vitro dissolution test and/or with respect to improved shelf life of the compositions upon storage.

The invention also relates to a particulate material obtained by the novel process and to pharmaceutical compositions containing such particulate material. The particulate material obtained exhibits excellent flowability and compactability and possess excellent tabletting properties.

BACKGROUND OF THE INVENTION

There is a need for developing new and improved methods which enable preparation of pharmaceutical compositions for oral use that release the active substance from the composition in a suitable manner to enable an absorption of the active substance into the circulatory system.

DETAILED DISCLOSURE OF THE INVENTION

The present invention provides a method for controlled agglomeration, i.e. a controlled growth in particle size of a particulate material. Controlled agglomeration is provided using a process for the preparation of a particulate material (see below).

The invention also provides a process for the preparation of a particulate material, the process comprising
  i) spraying a first composition comprising a carrier, which has a melting point of about 5° C. or more such as, e.g., about 10° C. or more, about 20° C. or more or about 25° C. or more and which is present in the first composition in liquid form, on a second composition comprising a material in solid form, the second composition having a temperature of at the most a temperature corresponding to the melting point of the carrier and/or of the carrier composition such as, e.g., a temperature of at least about 2° C., at least about 5° C. or at least about 10° C. lower than the melting point of the carrier and/or of the carrier composition, and
  ii) mixing or other means of mechanical working the second composition onto which the first composition is sprayed to obtain the particulate material.

The process enables incorporation in a solid material of a high load of a carrier of a type that e.g. due to its solubility properties enables a high load of therapeutically and/or prophylactically active substances with a relatively low aqueous solubility. The carrier is normally solid or semi-solid and normally it has a sticky, oily or waxy character. However, the carrier may also be fluid at room temperature or even at temperature below 5° C. and in such cases it is contemplated that the process is carried out by employment of cooling of the second composition. By employment of the novel controlled agglomeration method a particulate material with a high load of carrier may be prepared and the resulting particulate material appears as a particulate powder in solid form. The particulate material obtained by the novel method has excellent properties with respect to flowability, bulk density, compactability and thus, it is suitable for use in the preparation of e.g. tablets. Although the particulate material may have a high load of a carrier of substantially sticky character the particulate material prepared has minimal, if any, adherence to tablet punches and/or dies during manufacture of tablets.

Methods for the preparation of granular products are described e.g. in EP-A-0 306 465 (Lejus Medical Aktiebolag), JP 60184378 (Takeda) and in WO 01/22941 (H. Lundbeck A/S). However, in none of these documents is described a method for the preparation of a particulate material, which method enables incorporation of a relatively high amount of a carrier as defined below and at the same time controlling the size of the particles obtained.

Carriers and Carrier Compositions

As indicated above an important step in the process for the preparation of a particulate material according to the invention is the addition of a carrier or a carrier composition. The carrier is of a type, which has a melting point of at least about 25° C. such as, e.g., at least about 30° C. at least about 35° C. or at least about 40° C. For practical reasons, the melting point may not be too high, thus, the carrier normally has a melting point of at the most about 300° C. such as, e.g., at the most about 250° C., at the most about 200° C., at the most about 150° C. or at the most about 100° C. If the melting point is higher then it becomes very difficult to ensure maintenance of a sufficient high temperature during the delivery of the carrier to the spraying equipment necessary to provide the melted carrier (or carrier composition) in the form of a spray. Furthermore, in those cases where e.g. a therapeutically and/or prophylactically active substance is included in the carrier composition, a relatively high temperature may promote e.g. oxidation or other kind of degradation of the substance.

In the present context, the melting point is determined by DSC (Differential Scanning Calorimetry). The melting point is determined as the temperature at which the linear increase of the DSC curve intersect the temperature axis (see FIG. 8 for further details).

Suitable carriers are generally substances, which are used in the manufacture of pharmaceuticals as so-called melt binders or solid solvents (in the form of solid dosage form), or as co-solvents or ingredients in pharmaceuticals for topical use.

The carrier may be hydrophilic, hydrophobic and/or they may have surface-active properties. In general hydrophilic and/or hydrophobic carriers are suitable for use in the manufacture of a pharmaceutical composition comprising a therapeutically and/or prophylactically active substance that has a relatively low aqueous solubility and/or when the release of the active substance from the pharmaceutical composition is designed to be immediate or non-modified. Hydrophobic carriers, on the other hand, are normally used in the manufacture of a modified release pharmaceutical composition. The above-given considerations are simplified to illustrate general principles, but there are many cases where other combinations of carriers and other purposes are relevant and, therefore, the examples above should not in any way limit the invention.

Examples on a suitable carrier are a hydrophilic carrier, a hydrophobic carrier, a surfactant or mixtures thereof.

Typically, a suitable hydrophilic carrier is selected from the group consisting of: polyether glycols such as, e.g., polyethylene glycols, polypropylene glycols; polyoxyethylenes; polyoxypropylenes; poloxamers and mixtures thereof, or it may be selected from the group consisting of: xylitol, sorbitol, potassium sodium tartrate, sucrose tribehenate, glucose, rhamnose, lactitol, behenic acid, hydroquinon monomethyl ether, sodium acetate, ethyl fumarate, myristic acid, citric acid, Gelucire 50/13, other Gelucire types such as, e.g., Gelucire 44/14 etc., Gelucire 50/10, Gelucire 62/05, Sucro-ester 7, Sucro-ester 11, Sucro-ester 15, maltose, mannitol and mixtures thereof.

A hydrophobic carrier for use in a process of the invention may be selected from the group consisting of: straight chain saturated hydrocarbons, sorbitan esters, paraffins; fats and oils such as e.g., cacao butter, beef tallow, lard, polyether glycol esters; higher fatty acid such as, e.g. stearic acid, myristic acid, palmitic acid, higher alcohols such as, e.g., cetanol, stearyl alcohol, low melting point waxes such as, e.g., glyceryl monostearate, hydrogenated tallow, myristyl alcohol, stearyl alcohol, substituted and/or unsubstituted monoglycerides, substituted and/or unsubstituted diglycerides, substituted and/or unsubstituted triglycerides, yellow beeswax, white beeswax, carnauba wax, castor wax, japan wax, acetylate monoglycerides; NVP polymers, PVP polymers, acrylic polymers, or a mixture thereof.

In an interesting embodiment, the carrier is a polyethylene glycol having an average molecular weight in a range of from about 400 to about 35,000 such as, e.g., from about 800 to about 35,000, from about 1,000 to about 35,000 such as, e.g., polyethylene glycol 1,000, polyethylene glycol 2,000, polyethylene glycol 3,000, polyethylene glycol 4,000, polyethylene glycol 5,000, polyethylene glycol 6000, polyethylene glycol 7,000, polyethylene glycol 8,000, polyethylene glycol 9,000 polyethylene glycol 10,000, polyethylene glycol 15,000, polyethylene glycol 20,000, or polyethylene glycol 35,000. In certain situations polyethylene glycol may be employed with a molecular weight from about 35,000 to about 100,000.

In another interesting embodiment, the carrier is polyethylene oxide having a molecular weight of from about 2,000 to about 7,000,000 such as, e.g. from about 2,000 to about 100,000, from about 5,000 to about 75,000, from about 10,000 to about 60,000, from about 15,000 to about 50,000, from about 20,000 to about 40,000, from about 100,000 to about 7,000,000 such as, e.g., from about 100,000 to about 1,000,000, from about 100,000 to about 600,000, from about 100,000 to about 400,000 or from about 100,000 to about 300,000.

In another embodiment, the carrier is a poloxamer such as, e.g. Poloxamer 188, Poloxamer 237, Poloxamer 338 or Poloxamer 407 or other block copolymers of ethylene oxide and propylene oxide such as the Pluronic® and/or Tetronic® series. Suitable block copolymers of the Pluronic® series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic® F38, P65, P68LF, P75, F77, P84, P85, F87, F88, F98, P103, P104, P105, F108, P123, F123, F127, 10R8, 17R8, 25R5, 25R8 etc. Suitable block copolymers of the Tetronic series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature.

The carrier may also be a sorbitan ester such as, e.g., sorbitan di-isostearate, sorbitan dioleate, sorbitan monolaurate, sorbitan monoisostearate, sorbitan monooleate, sorbitan monopalmitate, sorbitan monostearate, sorbitan sesqui-isostearate, sorbitan sesquioleate, sorbitan sesquistearate, sorbitan tri-isostearate, sorbitan trioleate, sorbitan tristearate or mixtures thereof.

The carrier composition may of course comprise a mixture of different carriers such as, e.g., a mixture of hydrophilic and/or hydrophobic carriers.

In another interesting embodiment, the carrier is a surfactant or a substance having surface-active properties. It is contemplated that such substances are involved in the wetting of e.g. slightly soluble active substance and thus, contributes to improved solubility characteristics of the active substance.

Examples on surfactants are given in the following. In order to be suitable for use as a carrier, the criteria with respect to melting point and/or viscosity discussed herein must be fulfilled. However, the list below encompasses surfactants in general, because surfactants may also be added to the carrier composition in the form of pharmaceutically acceptable excipients.

In a process according to the invention, the carrier may be employed as such or in the form of a carrier composition. A carrier composition comprises one or more carriers optionally together with one or more other ingredients. Thus, the carrier composition may comprise a mixture of hydrophilic and/or hydrophobic carriers and/or surfactants. The carrier composition may also comprise one or more therapeutically and/or prophylactically active substances and/or one or more pharmaceutically acceptable excipients.

Suitable excipients for use in a carrier composition (and—as discussed above—for use as carriers it selves) are surfactants such as, e.g., hydrophobic and/or hydrophilic surfactants as those disclosed in WO 00/50007 in the name of Lipocine, Inc. Examples on suitable surfactants are i) polyethoxylated fatty acids such as, e.g. fatty acid mono- or diesters of polyethylene glycol or mixtures thereof such as, e.g. mono- or diesters of polyethylene glycol with lauric acid, oleic acid, stearic acid, myristic add, ricinoleic acid, and the polyethylene glycol may be selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, ii) polyethylene glycol glycerol fatty acid esters, i.e. esters like the above-mentioned but in the form of glyceryl esters of the individual fatty acids;

iii) glycerol, propylene glycol, ethylene glycol, PEG or sorbitol esters with e.g. vegetable oils like e.g. hydrogenated castor oil, almond oil, palm kernel oil, castor oil, apricot kernel oil, olive oil, peanut oil, hydrogenated palm kernel oil and the like, iv) polyglycerized fatty acids like e.g. polyglycerol stearate, polyglycerol oleate, polyglycerol ricinoleate, polyglycerol linoleate, v) propylene glycol fatty acid esters such as, e.g. propylene glycol monolaurate, propylene glycol ricinoleate and the like, vi) mono- and diglycerides like e.g. glyceryl monooleate, glyceryl dioleae, glyceryl mono- and/or dioleate, glyceryl caprylate, glyceryl caprate etc.;

vii) sterol and sterol derivatives;
viii) polyethylene glycol sorbitan fatty acid esters (PEG-sorbitan fatty acid esters) such as esters of PEG with the various molecular weights indicated above, and the various Tween® series;
ix) polyethylene glycol alkyl ethers such as, e.g. PEG oleyl ether and PEG lauryl ether;
x) sugar esters like e.g. sucrose monopalmitate and sucrose monolaurate;
xi) polyethylene glycol alkyl phenols like e.g. the Triton® X or N series:
xii) polyoxyethylene-polyoxypropylene block copolymers such as, e.g., the Pluronic® series, the Synperonic® series, Emkalyx®, Lutrol®, Supronic® etc. The generic term for these polymers is "poloxamers" and relevant examples in the present context are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407;
xiii) sorbitan fatty acid esters like the Span® series or Ariacel® series such as, e.g. sorbinan monolaurate, sorbitan monopalmitate, sorbitan monooleate, sorbitan monostearate etc.;
xiv) lower alcohol fatty acid esters like e.g. oleate, isopropyl myristate, isopropyl palmitate etc.;
xv) ionic surfactants including cationic, anionic and zwitterionic surfactants such as, e.g. fatty acid salts, bile salts, phospholipids, phosphoric acid esters, carboxylates, sulfates and sulfonates etc.

When a surfactant or a mixture of surfactants is present in a carrier composition the concentration of the surfactant(s) is normally in a range of from about 0.1–75% w/w such as, e.g., from about 0.1 to about 20% w/w, from about 0.1 to about 15% w/w, from about 0.5 to about 10% w/w, or alternatively, when applicable as a carrier or a part of the carrier composition from about 20 to about 75% w/w such as, e.g. from about 25 to about 70% w/w, from about 30 to about 60% w/w.

Other suitable excipients in a carrier composition may be solvents or semi-solid excipients like, e.g. propylene glycol, polyglycolised glycerides including Gelucire 44/14, complex fatty materials of plant origin including theobroma oil, carnauba wax, vegetable oils like e.g. almond oil, coconut oil, corn oil, cottonseed oil, sesame oil, soya oil, olive oil, castor oil, palm kernels oil, peanut oil, rape oil, grape seed oil etc., hydrogenated vegetable oils such as, e.g. hydrogenated peanut oil, hydrogenated palm kernels oil, hydrogenated cottonseed oil, hydrogenated soya oil, hydrogenated castor oil, hydrogenated coconut oil; natural fatty materials of animal origin including beeswax, lanolin, fatty alcohols including cetyl, stearyl, lauric, myristic, palmitic, stearic fatty alcohols; esters including glycerol stearate, glycol stearate, ethyl oleate, isopropyl myristate; liquid interesterified semi-synthetic glycerides including Miglycol 810/812; amide or fatty acid alcolamides including stearamide ethanol, diethanolamide of fatty coconut acids etc.

Other additives in the carrier composition may be antioxidants like e.g. ascorbic acid, ascorbyl palmitate, butylated hydroxyanisole, butylated hydroxytoluene, hypophosphorous acid, monothioglycerol, potassium metabisulfite, propyl gallate, sodium formaldehylde sulfoxylate, sodium metabisulfite, sodium thiosulfate, sulfur dioxide, tocopherol, tocopherol acetate, tocopherol hemisuccinate, TPGS or other tocopherol derivatives, etc. The carrier composition may also contain e.g. stabilising agents. The concentration of an antioxidant and/or a stabilizing agent in the carrier composition is normally from about 0.1% w/w to about 5% w/w.

In those cases where a carrier composition is employed, the requirements with respect to the melting point mentioned above normally also apply to the carrier composition, especially in those cases where a minor amount of water is included in the carrier composition. However, when the carrier composition is heated the carrier composition may be in the form of two or more phases (e.g. two distinct liquid phase, or a liquid phase comprising e.g. an active substance dispersed therein). In such cases, the melting point is not a true melting point but merely a heating point where the carrier composition becomes in a liquid form, which is suitable for use in a spraying device. Often such a heating point will for practical purposes correspond to the melting point of the carrier itself.

The total concentration of carrier(s) in the carrier composition is normally in a range of from about 5 to about 100% w/w such as, e.g., from about 10 to about 99.5% w/w, from about 15 to about 99% w/w, from about 15 to about 98% w/w, from about 15 to about 97% w/w, from about 20 to about 95% w/w such as at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, at least about 80% w/w, at least about 85% w/w, at least about 90% w/w, at least about 95% w/w or at least about 98% w/w.

As explained above, in a process according to the invention the carrier or the carrier composition is brought on liquid form by heating the carrier and/or the carrier composition to a temperature, which causes the carrier and/or the carrier composition to melt, and the carrier in liquid form (i.e. as a solution or a dispersion) is sprayed on the second composition.

As mentioned above, the carrier or the carrier composition in melted or liquidized form is sprayed on a second composition. Thus, the carrier or the carrier composition should have a suitable viscosity. If the viscosity is too high, the carrier or carrier composition will be too "thick" and will have a tendency of adhering to the nozzle, which may result in that the delivery through the nozzle is stopped. For the present purpose a viscosity of the carrier and/or the carrier composition is suitably if the viscosity (Brookfield DV-III) is at the most about 800 mPas at a temperature of at the most 100° C. such as, e.g., at the most 700, at the most 600, at the most 500 mPas. In those cases where the melting point of the carrier or the carrier composition is more than about 80° C., the viscosity values mentioned above are at a temperature of about 40° C. above the melting point.

In the particulate material obtained by a process according to the invention, the concentration of the carrier is from about 5 to about 95% w/w such as, e.g. from about 5 to about 90% w/w, from about 5 to about 85% w/w, from about 5 to about 80% w/w, from about 10 to about 75% w/w, from about 15 to about 75% w/w, from about 20 to abut 75% w/w, from about 25% to about 75% w/w, from about 30% to about 75% w/w. from about 35% to about 75% w/w, from about 25% to about 70% w/w, from about 30% to about 70% w/w, from about 35% to abut 70% w/w. from about 40% to about 70% w/w, from about 45% to about 65% w/w or from about 45% to about 60% w/w.

In those cases where the second composition comprises a pharmaceutically acceptable excipient that has a relatively high particle density it is preferred that the concentration of the carrier in the particulate material obtained by a process of the invention is from about 5 to about 95% v/v such as, e.g. from about 5 to about 90% v/v, from about 5 to about 85% v/v, from about 5 to about 80% v/v, from about 10 to about 75% v/v from about 15 to about 75% v/v, from about 20 to abut 75% v/v, from about 25% to about 75% v/v, from about 30% to about 75% v/v, from about 35% to about 75% v/v, from about 25% to about 70% v/v, from about 30% to about 70% v/v, from about 35% to abut 70% v/v, from about 40% to about 70% v/v, from about 45% to about 65% v/v or from about 45% to about 60% v/v.

In the following is given a calculation example:

Recalculation from % w/w to % vv (of total composition):

Particle density of lactose: 1.56 g/cm$^3$

Particle density of calcium hydrogen phosphate anhydrous: 2.89 g/cm$^3$

Particle density of PEG 6000: 1.17 g/cm$^3$

For lactose: w/w ratio of 50% PEG 6000/(lactose+PEG 6000) equals a % v/v of 56% For calcium hydrogen phosphate anhydrous: w/w ratio of 50% PEG 6000/(calcium hydrogen phosphate anhydrous+PEG 6000) equals a % v/v of 71%.

In many cases it is suitable to dissolve or disperse a therapeutically and/or prophylactically active substance in the carrier or in the carrier composition. Suitable therapeutically and/or prophylactically active substances are discussed below.

In a process according to the invention it is not necessary to employ water or an aqueous medium e.g. together with a binder in order to build up agglomerates of a suitable size. The agglomeration suitably takes place under water-free or substantially water-free conditions. Thus, the process is also very useful when active substances or other ingredients are employed which are susceptible to water (e.g. degradation under aqueous conditions). However, if desired, water or an aqueous medium may of course be incorporated in the carrier composition. Although the carrier composition normally is essentially non-aqueous, water may be present to a certain extent and then the concentration of water in the carrier composition is the most about 20% w/w water such as at the most about 15% w/w, at the most abut 10% w/w, at the most about 5% w/w or at the most about 2.5% w/w.

Therapeutically and/or Prophylactically Active Substances

In a preferred embodiment of the invention the particulate material obtained by a process according to the invention comprises a therapeutically and/or prophylactically active substance. The particulate matter may also or alternatively comprise a cosmetically active substance (i.e. a substance that is employed in cosmetic compositions). In a process according to the invention the active substance may be included in the carrier composition and/or in the second composition.

In the present context a therapeutically and/or prophylactically active substance includes any biologically and/or physiologically active substance that has a function on an animal such as, e.g. a mammal like a human. The term includes drug substances, hormones, genes or gene sequences, antigen-comprising material, proteins, peptides, nutrients like e.g. vitamins, minerals, lipids and carbohydrates and mixtures thereof. Thus, the term includes substances that have utility in the treatment and/or preventing of diseases or disorders affecting animals or humans, or in the regulation of any animal or human physiological condition. The term also includes any biologically active substance which, when administered in an effective amount, has an effect on living cells or organisms.

Many active substances have and it is expected that many of the future drug substances will have undesired properties especially with respect to water solubility and to oral bioavailability. Therefore, a novel technology, which enables especially therapeutically and/or prophylactically active substances to be delivered to the body in a relatively easy manner and at the same time enables the desired therapeutic and/or prophylactic response, is highly needed.

By employment of a process according to the present invention it is contemplated that this object can be achieved for many such substances, especially in view of the promising results the inventors have obtained from a study in Beagle dogs. Accordingly, the present inventors have found very promising results with respect to bioavailability when a process according to the invention is employed for the preparation of particulate material containing an active substance with a very low aqueous solubility. Thus, a process according to the invention is especially suitable for use for the preparation of particulate material comprising an active substance that has an aqueous solubility at 25° C. and pH of 7.4 of at the most about 3 mg/ml such as, e.g., at the most about 2 mg/ml, at the most about 1 mg/ml, at the most about 750 µg/ml, at the most about 500 µg/ml, at the most about 250 µg/ml, at the most about 100 µg/ml, at the most about 50 µg/ml, at the most about 25 µg/ml, at the most about 20 µg/ml or at the most about 10 µg/ml. In specific embodiments the solubility of the active substance may be much lower such as, e.g., at the most about 1 µg/ml, at the most about 100 µg/ml, at the most about 75 µg/ml such as about 50 µg/ml.

As mentioned above a process according to the invention may advantageously be carried out without employment of water or an aqueous medium. Thus, the process is especially suitable for use for active substances that are degraded, decomposed or otherwise influenced by water.

Examples on active substances suitable for use in a particulate material according to the invention are in principle any active substance such as, e.g. freely water soluble as well as more slightly or insoluble active substances. Thus, examples on active substances suitable for use are e.g. antibacterial substances, antihistamines and decongestants, anti-inflammatory agents, antiparasitics, antivirals, local anesthetics, antifungals, amoebicidals or trichomonocidal agents, analgesics, antianxiety agents, anticlotting agents, antiarthritics, antiasthmatics, antiarthritic, anticoagulants, anticonvulsants, antidepressants, antidiabetics, antiglaucoma agents, antimalarials, antimicrobials, antineoplastics, antiobesity agents, antipsychotics, antihypertensives, antitussives, auto-immune disorder agents, anti-impotence agents, anti-Parkinsonism agents, anti-Alzheimers' agents, antipyretics, anticholinergics, anti-ulcer agents, anorexic, beta-blockers, beta-2 agonists, beta agonists, blood glucose-lowering agents, bronchodilators, agents with effect on the central nervous system, cardiovascular agents, cognitive enhancers, contraceptives, cholesterol-reducing agents, cytostatics, diuretics, germicidals, H-2 blockers, hormonal agents, hypnotic agents, inotropics, muscle relaxants, muscle contractants, physic energizers, sedatives, sympathomimetics, vasodilators, vasoconstrictors, tranquilizers, electrolyte supplements, vitamins, counterirritants, stimulants, anti-hormones, drug antagonists, lipid-regulating agents, uricosurics, cardiac glycosides, expectorants, purgatives, contrast materials, radiopharmaceuticals, imaging agents, peptides, enzymes, growth factors, etc.

Specific examples include e.g.

Anti-inflammatory drugs like e.g. ibuprofen, indometacin, naproxen, nalophine;

Anti-Parkinsonism agents like e.g. bromocriptine, biperidin, benzhexol, benztropine etc.

Antidepressants like e.g. imipramine, nortriptyline, pritiptyline, etc.

Antibiotics like e.g. clindamycin, erythomycin, fusidic acid, gentamicin, mupirocine, amfomycin, neomycin, metronidazol, sulphamethizole, bacitracin, framycetin, polymyxin B, acitromycin etc, Antifungal agents like e.g. miconazol, ketoconaxole, clotrimazole, amphotericin B, nystatin, mepyramin, econazol, fluconazol, flucytocine, griseofulvin, bifonazole, amorofine, mycostatin, itrconazole, terbenafine, terconazole, tolnaftate etc.

Antimicrobial agents like e.g. metronidazole, tetracyclines, oxytetracylines, peniciilins etc.

Antiemetics like e.g. metoclopramide, droperidol, haloperidol, promethazine etc.

Antihistamines like e.g. chlorpheniramine, terfenadine, triprolidine etc.

Antimigraine agents like e.g. dihydroergotamine, ergotamine, pizofylline etc.

Coronary, cerebral or peripheral vasodilators like e.g. nifedipine, diltiazem etc.

Antianginals such as, e.g., glyceryl nitrate, isosorbide dinitrate, molsidomine, verapamil etc.

Calcium channel blockers like e.g. verapamil, nifedipine, diltiazem, nicardipine etc.

Hormonal agents like e.g. estradiol, estron, estriol, polyestradiol, polyestriol, dienestrol, diethylstilbestrol, progesterone, dihydroprogesterone, cyprosterone, danazol, testosterone etc.

Contraceptive agents like e.g. ethinyl estradiol, lynestrenol, etynodiol, norethisterone, mestranol, norgestrel, levonorgestrel, desodestrel, medroxyprogesterone etc.

Antithrombotic agents like e.g. heparin, warfarin etc.

Diuretics like e.g. hydrochlorothiazide, flunarizine, minoxidil etc.

Antihypertensive agents like e.g. propanolol, metoprolol, clonidine, pindolol etc.

Corticosteroids like e.g. beclomethasone, betamethasone, betamethasone-17-valerate, betamethasone-dipropionate, clobetasol, clobetasol-17-butyrate, clobetasol-propionate, desonide, desoxymethasone, dexamethasone, diflucortolone, flumethasone, flumethasone-pivalte, fluocinolone acetonide, fluocinoide, hydrocortisone, hydrocortisone-17-butyrate, hydrocortisonebuteprate, methylprednisolone, triamcinolone acetonide, hacinonide, fluprednide acetate, alklometasone-dipropionate, fluocortolone, fluticasonpropionte, mometasone-furate, desoxymethasone, diflurason-diacetate, halquinol, cliochinol, chlorchinaldol, fluocinolone-acetonide etc.

Dermatological agents like e.g. nitrofurantoin, dithranol, clioquinol, hydroxyquinoline, isotretionin, methoxsalen, methotrexate, tretionin, trioxalen, salicylic add, penicillamine etc.

Steroids like e.g. estradiol, progesterone, norethindrone, levonorgestrel, ethynodiol, levonorgestrol, norgestimate, gestanin, desogestrel, 3-keton-desogesterel, demegestone, promethoestrol, testosterone, spironolactone and esters thereof etc.

Nitro compounds like e.g. amyl nitrates, nitroglycerine and isosorbide nitrate etc.

Opioids like e.g. morphine, buprenorphine, oxymorphone, hydromorphone, codeine, tramadol etc.

Prostaglandins such as, e.g., a member of the PGA, PGB, PGE or PGF series such as, e.g. minoprostol, dinoproston, carboprost, eneprostil etc.

Peptides like e.g. growth hormone releasing factors, growth factors (e.g. epidermal growth factor (EGF), nerve growth factor (NGF), TGF, PDGF, insulin growth factor (IGF), fibroblast growth factor (aFGF, bFGF etc.), somatostatin, calcitonin, insulin, vasopressin, interferons, IL-2 etc., urokinase, serratiopeptidase, superoxide dismutase, thyrotropin releasing hormone, lutenizing hormone releasing hormone (LH-RH), corticotrophin releasing hormone; growth hormone releasing hormone (GHRH), oxytodin, erythropoietin (EPO), colony stimulating factor (CSF) etc.

Interesting examples on active substances that are slightly soluble, sparingly soluble or insoluble in water are given in the following tables:

TABLE 1

Poorly-Soluble Drug Candidates

| Drug Name | Therapeutic Class | Solubility In Water |
|---|---|---|
| Alprazolam | CNS | Insoluble |
| Amiodarone | Cardiovascular | Very Slightly |
| Amlodipine | Cardiovascular | Slightly |
| Astemizole | Respiratory | Insoluble |
| Atenolol | Cardiovascular | Slightly |
| Azathioprine | Anticancer | Insoluble |
| Azelastine | Respiratory | Insoluble |
| Beclomethasone | Respiratory | Insoluble |
| Budesonide | Respiratory | Sparingly |
| Buprenorphine | CNS | Slightly |
| Butalbital | CNS | Insoluble |
| Carbamazepine | CNS | Insoluble |
| Carbidopa | CNS | Slightly |
| Cefotaxime | Anti-infective | Sparingly |
| Cephalexin | Anti-infective | Slightly |
| Cholestyramine | Cardiovascular | Insoluble |
| Ciprofloxacin | Anti-infective | Insoluble |
| Cisapride | Gastrointestinal | Insoluble |
| Cisplatin | Anticancer | Slightly |
| Clarithromycin | Anti-infective | Insoluble |
| Clonazepam | CNS | Slightly |
| Clozapine | CNS | Slightly |
| Cyclosporin | Immunosuppressant | Practically Insoluble |
| Diazepam | CNS | Slightly |
| Diclofenac sodium | NSAID | Sparingly |
| Digoxin | Cardiovascular | Insoluble |
| Dipyridamole | Cardiovascular | Slightly |
| Divalproex | CNS | Slightly |
| Dobutamine | Cardiovascular | Sparingly |
| Doxazosin | Cardiovascular | Slightly |
| Enalapril | Cardiovascular | Sparingly |
| Estradiol | Hormone | Insoluble |
| Etodolac | NSAID | Insoluble |
| Etoposide | Anticancer | Very Slightly |
| Famotidine | Gastrointestinal | Slightly |
| Felodipine | Cardiovascular | Insoluble |
| Fentanyl citrate | CNS | Sparingly |
| Fexofenadine | Respiratory | Slightly |
| Finasteride | Genito-urinary | Insoluble |
| Fluconazole | Antifungal | Slightly |
| Flunosolide | Respiratory | Insoluble |
| Flurbiprofen | NSAID | Slightly |
| Fluvoxamine | CNS | Sparingly |
| Furosemide | Cardiovascular | Insoluble |
| Glipizide | Metabolic | Insoluble |
| Glyburide | Metabolic | Sparingly |
| Ibuprofen | NSAID | Insoluble |
| Isosorbide dinitrate | Cardiovascular | Sparingly |
| Isotretinoin | Dermatological | Insoluble |
| Isradipine | Cardiovascular | Insoluble |
| Itraconzole | Antifungal | Insoluble |
| Ketoconazole | Antifungal | Insoluble |
| Ketoprofen | NSAID | Slightly |
| Lamotrigine | CNS | Slightly |

TABLE 1-continued

Poorly-Soluble Drug Candidates

| Drug Name | Therapeutic Class | Solubility In Water |
|---|---|---|
| Lansoprazole | Gastrointestinal | Insoluble |
| Loperamide | Gastrointestinal | Slightly |
| Loratadine | Respiratory | Insoluble |
| Lorazepam | CNS | Insoluble |
| Lovastatin | Cardiovascular | Insoluble |
| Medroxyprogesterone | Hormone | Insoluble |
| Mefenamic acid | Analgesic | Slightly |
| Methylprednisolone | Steroid | Insoluble |
| Midazolam | Anesthesia | Insoluble |
| Mometasone | Steroid | Insoluble |
| Nabumetone | NSAID | Insoluble |
| Naproxen | NSAID | Insoluble |
| Nicergoline | CNS | Insoluble |
| Nifedipine | Cardiovascular | Practically Insoluble |
| Norfloxacin | Anti-infective | Slightly |
| Omeprazole | Gastrointestinal | Slightly |
| Paclitaxel | Anticancer | Insoluble |
| Phenytoin | CNS | Insoluble |
| Piroxicam | NSAID | Sparingly |
| Quinapril | Cardiovascular | Insoluble |
| Ramipril | Cardiovascular | Insoluble |
| Risperidone | CNS | Insoluble |
| Saquinavir | Protease inhibitor | Practically Insoluble |
| Sertraline | CNS | Slightly |
| Simvastatin | Cardiovascular | Insoluble |
| Terbinafine | Antifungal | Slightly |
| Terfenadine | Respiratory | Slightly |
| Triamcinolone | Steroid | Insoluble |
| Valproic acid | CNS | Slightly |
| Zolpidem | CNS | Sparingly |

The amount of active substance incorporated in a particulate material (and/or in a pharmaceutical, cosmetic or food composition) may be selected according to known principles of pharmaceutical formulation. In general, the dosage of the active substance present in a particulate material according to the invention depends inter alia on the specific drug substance, the age and condition of the patient and of the disease to be treated.

A particulate material according to the invention may comprise a cosmetically active ingredient and/or a food ingredient. Specific examples include vitamins, minerals, vegetable oils, hydrogenated vegetable oils, etc.

Second Composition

As mentioned above the carrier or carrier composition is sprayed on a second composition. In order to be able to achieve a high amount of carrier in the final particulate material and in order to enable a controlled agglomeration of the particles comprised in the second composition, the present inventors have surprisingly found that in specific embodiments, the second composition should initially have a temperature which is at least about 10° C. such as, e.g., at least about 15° C., at least about 20° C., at least about 25° C., or at least about 30° C. below the melting point of the carrier or carrier composition (or, as discussed above, the heating point of the carrier composition). However, as mentioned above, a temperature difference of at least about 10° C. it is not always necessary. Thus, the second composition may have a temperature of at the most a temperature corresponding to the melting point of the 2° C., at least about 5° C. No external heating of the second composition is normally employed during the process of the invention, but in some cases it may be advantageous to employ a cooling

TABLE 2

Poorly-Soluble Drugs with Low Bioavailability

| Drug Name | Indication | Solubility In Water | Bioavailability |
|---|---|---|---|
| Astemizole | Allergic Rhinitis | Insoluble | Low–moderate |
| Cyclandelate | Peripheral vascular disease | Insoluble | Low |
| Perphenazine | Psychotic disorder | Insoluble | Low |
| Testosterone | Androgen Replacement Therapy | Insoluble | Low |
| Famotidine | GERD | Slightly soluble | Low (39–50%) |
| Budesonide | Allergic Rhinitis | Sparingly soluble | Low (~15%) |
| Mesalamine | Irritable Bowel Syndrome | Slightly soluble | Low (~20%) |
| Clemastine fumarate | Allergic Rhinitis | Slightly soluble | Low (~39%) |
| Buprenorphine | Pain | Slightly soluble | Low (<30%) |
| Sertraline | Anxiety | Slightly soluble | Low (<44%) |
| Auranofin | Arthritis | Slightly soluble | Low (15–25%) |
| Felodipine | Hypertension | Insoluble | Low (15%) |
| Isradipine | Hypertension | Insoluble | Low (15–24%) |
| Danazol | Endometriosis | Insoluble | Low |
| Loratadine | Allergic Rhinitis | Insoluble | Low |
| Isosorbide dinitrate | Angina | Sparingly soluble | Low (20–35%) |
| Fluphenazine | Psychotic disorder | Insoluble | Low (2–3%) |
| Spironolactone | Hypertension, Edema | Insoluble | Low (25%) |
| Biperiden | Parkinson's disease | Sparingly soluble | Low (29–33%) |
| Cyclosporin | Transplantation | Slightly soluble | Low (30%) |
| Norfloxacin | Bacterial Infection | Slightly soluble | Low (30–40%) |
| Cisapride | GERD | Insoluble | Low (35–40%) |
| Nabumetone | Arthritis | Insoluble | Low (35%) |
| Dronabinol | ANTIEMETIC | Insoluble | Low 10–20%) |
| Lovastatin | Hyperlipidemia | Insoluble | Low (~5%) |
| Simvastatin | Hyperlipidemia | Insoluble | Low (<5%) | via the inlet air. However, the temperature of the second composition may increase to a minor extent due to the working of the composition. However, the temperature must (or will) not be higher than at the most the melting point of the carrier or carrier composition such as, e.g. at the most about 5° C. such as at the most about 10° C., at the most about 15° C. or at the most about 20° C. below the melting point of the carrier or the carrier composition. Accordingly, a process of the invention can be carried out without any heating of the second composition, i.e. it can be carried out at ambient or room temperature (i.e. normally in a range of from about 20° C. to about 25° C.).

In contrast thereto, known melt granulation methods involve external heating of the material that is to be granulated (or agglomerated) together with a melt binder.

The second composition comprises pharmaceutically and/or cosmetically acceptable excipients and, furthermore, a therapeutically and/or prophylactically active substance may be present in the second composition.

In the present context the terms "pharmaceutically acceptable excipient" and "cosmetically acceptable excipient" are intended to denote any material, which is inert in the sense that i substantially does not have any therapeutic and/or prophylactic effect per se. Such an excipient may be added with the purpose of making it possible to obtain a pharmaceutical and/or cosmetic composition, which has acceptable technical properties.

Examples on suitable excipients for use in a second composition include fillers, diluents, disintegrants, binders, lubricants etc. or mixture thereof. As the particulate material obtained by a process according to the invention may be used for different purposes, the choice of excipients is normally made taken such different uses into considerations. Other pharmaceutically acceptable excipients for use in a second composition (and/or in the carrier composition) are e.g. acidifying agents, alkalizing agents. preservatives, antioxidants, buffering agents, chelating agents, coloring agents, complexing agents, emulsifying and/or solubilizing agents, flavors and perfumes, humectants, sweetening agents, wetting agents etc.

Examples on suitable fillers, diluents and/or binders include lactose (e.g. spray-dried lactose, α-lactose, β-lactose, Tabletose®, various grades of Pharmatose®, Microtose® or Fast-Floc®), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Specific examples of diluents are e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants are e.g. alginic acid or alginates, microcrystalline cellulose, hydroxypropyl cellulose and other cellulose derivatives, croscarmellose sodium, crospovidone, polacrillin potassium, sodium starch glycolate,.starch, pregelatinized starch, carboxymethyl starch (e.g. Primogel® and Explotab®) etc.

Specific examples of binders are e.g. acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch etc.

Glidants and lubricants may also be included in the second composition. Examples include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients which may be included in the second composition (and/or in the carrier composition) are e.g. colouring agents, taste-masking agents, pH-adjusting agents, solubilizing agents, stabilising agents, wetting agents, surface active agents, antioxidants, agents for modified release etc.

In certain cases it may be advantageously to incorporate a magnesium aluminometasilicate in the particulate material. It may be a part of the second composition or it may be added subsequently in order to facilitate a further processing of the particulate material (e.g. to prepare solid dosage forms like capsules or tablet). Magnesium aluminometasilicate is sold under the name Neusilin and is obtainable from Fuji Chemical Industries. Neusilin is normally used in order to improve filling capacity and compression property of powders and granules when added. Neusilin is also believed to reduce weight variation and to improve hardness and disintegration of tablets. Finally, Neusilin has an adsorption capability, which makes it suitable for use when processing waxy materials like oil extracts and waxes into pharmaceutical composition. Especially Neusilin UFL2 and US2 are said to be suitable for such a use.

Thus, in one aspect the invention relates to a process, wherein the second composition comprises magnesium aluminosilicate and/or magnesium aluminometasilicate such as, e.g, Neusilin S1, Neusilin FH2, Neusilin US2, Neusilin UFL2 or the like. Other suitable substances are contemplated to be bentonite, kaolin, magnesium trisilicate, montmorillonite and/or saponite. In a still further embodiment, the second composition comprises magnesium aluminosilicate and/or magnesium aluminometasilicate such as, e.g, Neusilin, and the particulate material obtained has an content of carrier of at least about 30% vv such as, e.g, at least about 40% v/v, at Yeast about 50% v/v, at least about 60% v/v, at least about 70% v/v, at least about 75% v/v, at least about 80% v/v, at least about 85% v/v or at least about 90% v/v.

Besides the known use of Neusilin, the present inventors have found that specific qualities of magnesium aluminometasilicate (Neusilin) have excellent properties as glidants or anti-adhesive most likely due to the porous structure of Neusilin. Thus, Neusilin may advantageously be added in order to reduce any adherence of the particulate material to the manufacturing equipment in particular to the tabletting machine. In the examples herein is given a comparison of the anti-adhesive properties of Neusilin compared with known lubricants and Neusilin seems to be a very promising and novel candidate as a lubricant.

Details on Controlled Agglomeration

A process according to the invention may be carried out in a high or low shear mixer or in a fluid bed. Important characteristics are that the carrier or the carrier composition is sprayed on the second composition, which is loaded into the mixer or the fluid bed. Normally, the carrier or the carrier composition is heated to a temperature above the melting point of the carrier and/or the carrier composition and the second composition has not been subject to any heating and has normally ambient temperature. The difference in temperature between the carrier and the second composition makes the carrier solidify rapidly which in turn leads to a controlled growth of the particle size. Thus, the inventors have found that by employing such conditions it is possible to control the agglomeration process so that the growth in particle size is controlled.

In the present context, the term "controlled agglomeration" is intended to mean that the increase in mean geometric diameter of a material is a linear or approximated linear function of the carrier concentration in the carrier composition (see FIG. 1). Controlled agglomeration is also present if a $d_{gw}$ of < or =500 μm is obtained when a carrier composition containing 20% carrier has been added to a second composition.

The possibility of controlling the agglomeration makes it possible to obtain a particulate material that has a very high load of carrier(s)—much higher than described when conventional methods like e.g. melt granulation is employed. As discussed above, a high load of carrier has shown to be of importance especially when particulate material is prepared containing a slightly water-soluble, sparingly water soluble or insoluble active substances. FIG. 2 is a theoretically calculated curve showing the relationship between obtainable dose and drug solubility in a carrier composition at different carrier concentrations in the particulate material assuming a total composition weight of 500 mg. It is seen that the dose can be increased by a factor of about 3.5 by increasing the concentration of carrier from 20% to 70%. By conventional melt granulation, i.e. a process by which heating of a melt binder and excipients is performed, normally a load of at the most about 15% w/w of the melt binder is obtained (calculated on the final composition). Another granulation method, which makes use of the same temperature of the binder and the material to be granulated, is a conventional granulation process, which is performed either by a wet or a dry granulation process.

A SEM micrograph in FIG. 3 shows a particulate material prepared by a process according to the present invention. PEG 6000 is used as a carrier and lactose is used as the second composition. The figure shows that the primary particles of lactose are agglomerated by immersion in the droplets of PEG 6000 or by coalescence between larger agglomerates. The agglomerates are partly coated with PEG 6000. The probability of agglomerate growth by coalescence is reduced by rapidly solidifying PEG due to the product temperature being kept at a minimum of 10° C. below the melting point of PEG.

In contrast thereto, uncontrolled agglomeration is shown in a SEM micrograph in FIG. 4. The particulate material is prepared according to Example 2 herein (uncontrolled agglomeration) using PEG 6000 as carrier and lactose as excipients. The figure shows that the particulate material has larger agglomerates with surplus of liquefied PEG at the surface of the agglomerates increasing the probability of agglomerate growth by coalescence at elevated product temperature.

A process according to the invention may be carried out in a fluid bed. In such cases the second composition is normally kept in a fluidized state by incoming air at ambient temperature. The carrier or carrier composition is sprayed on the fluidized second composition and in order to keep the carrier or carrier composition on a liquid form and/or to avoid any clotting of the spraying device, the spraying device is kept at a suitable temperature above the melting point of the carrier or carrier composition. Normally, the spraying is performed through a spraying device equipped with temperature controlling means.

The particulate material obtained by a process of the invention has a geometric weight mean diameter $d_{gw}$ of $\geq 10$ μm such as, e.g, 220 μm, from about 20 to about 2000, from about 30 to about 2000, from about 50 to about 2000, from about 60 to about 2000, from about 75 to about 2000 such as, e.g. from about 100 to about 1500 μm, from about 100 to about 1000 μm or from about 100 to about 700 μm. In specific embodiments the geometric weight mean diameter $d_{gw}$ is at the most about 400 μm or at the most 300 μm such as, e.g., from about 50 to about 400 μm such as, e.g., from about 50 to about 350μm, from about 50 to about 300 μm, from about 50 to about 250 μm or from about 100 to about 300 μm.

Particulate Material—Characteristics

Many characteristics of the particulate material obtained by a process according to the invention have already been discussed. In summary, a particulate material has good tabletting properties including good flowability and compactability. It has no or minimal adherence to the tabletting equipment either in itself or after addition of the normal amount of lubricants. It is an excellent alternative for incorporation of active substances with very low water solubility and/or with a very low bioavailability, or active substances, which are subject to degradation in the presence of water (the process may be carried out without any water).

Thus, a particulate material of the invention is excellent for a further processing into e.g. tablets. In contrast to capsules, tablets are normally easier and cheaper to produce and tablets are often preferred by the patient. Furthermore, a tablet formulation is relatively easy to adjust to specific requirements, e.g. with respect to release of the active substance, size etc.

The particulate material may also be coated (see Examples) with a film coating, an enteric coating, a modified release coating, a protective coating, an anti-adhesive coating etc.

Suitable coating materials are e.g. methylcellulose, hydroxypropylmethylcellulose, hydroxypropylcellulose, acrylic polymers, ethylcellulose, cellulose acetate phthalate, polyvinyl acetate phthalate, hydroxypropyl methylcellulose phthalate, polyvinylalcohol, sodium carboxymethylcellulose, cellulose acetate, cellulose acetate phthalate, gelatin, methacrylic acid copolymer, polyethylene glycol, shellac, sucrose, titanium dioxide, carnauba wax, microcrystalline wax, zein.

Plasticizers and other ingredients may be added in the coating material. The same or different active substance may also be added in the coating material.

Pharmaceutical Compositions

The particulate material obtained by a process according to the invention may be used as such or it may be further processed to the manufacture of a pharmaceutical and/or a cosmetic composition by addition of one or more suitable pharmaceutically and/or cosmetically acceptable excipients. Furthermore, the particulate material obtained may be provided with a coating to obtain coated particles, granules or pellets. Suitable coatings may be employed in order to obtain composition for immediate or modified release of the active substance and the coating employed is normally selected from the group consisting of film-coatings (for immediate or modified release) and enteric coatings or other kinds of modified release coatings, protective coatings or anti-adhesive coatings The particulate material obtained by a process of the invention is especially suitable for further processing into tablets. The material possesses suitable properties for tabletting purposes, cf. below, but in some cases it may be suitable to add further therapeutically and/or prophylactically active substances and/or excipients to the particulate material before the manufacture of tablets. For examples, by using a mixture of i) an active substance contained in modified release coated granules or granules in the form of modified release matrices and ii) an active substance in freely accessible form, a suitable release pattern can be designed in order to obtain a relatively fast release of an active substance followed by a modified (i.e. often prolonged) release of the same or a different active substance.

As appears from the above, a particulate material obtained by a process of the invention is suitable for use in the manufacture of tablets obtained by direct compression. Furthermore, the particulate material may in itself be employed as a binding agent for use in dry granulation processes.

A particulate material obtained by a process according to the invention may be employed in any kind of pharmaceutical compositions in which the use of a solid particulate material is applicable. Thus, relevant pharmaceutical compositions are e.g. solid, semi-solid, fluid or liquid composition or compositions in the form of a spray. The particulate material may also be incorporated in a suitable drug delivery device such as, e.g. a transdermal plaster, a device for vaginal use or an implant.

Solid compositions include powders, and compositions in dosage unit form such as, e.g. tablets, capsules, sachets, plasters, powders for injection etc.

Semi-solid compositions include compositions like ointments, creams, lotions, suppositories, vagitories, gels, hydrogels, soaps, etc.

Fluid or liquid compositions include solutions, dispersions such as, e.g., emulsions, suspension, mixtures, syrups, etc.

Accordingly, the invention also relates to any pharmaceutical composition comprising a particulate material obtainable by a process of the invention.

Other Aspects of the Invention

The invention also relates to a pharmaceutical particulate material obtained by mixing a first and a second composition as defined herein and heating to a temperature that is below the melting point of a carrier contained in the first composition. The heating may be applied while mixing or in a separate step. The particulate material generally has a geometric weight mean diameter $d_{gw}$ of $\geq 10$ μm such as, e.g. $\geq 20$ μm, from about 20 to about 2000, from about 30 to about 2000, from about 50 to about 2000, from about 60 to about 2000, from about 75 to about 2000 such as, e.g. from about 100 to about 1500 μm, from about 100 to about 1000 μm or from about 100 to about 700 μm, or at the most about 400 μm or at the most 300 μm such as, e.g., from about 50 to about 400 μm such as, e.g., from about 50 to about 350 μm, from about 50 to about 300 μm, from about 50 to about 250 μm or from about 100 to about 300 μm. In such a material the concentration of the carrier typically is at least about 40% v/v.

Such a particulate material is especially suitable for use in the preparation of solid dosage form such as tablets, capsules, sachets and the like. It may have sufficient properties with respect to flowability and/or anti-adhesion so that addition of e.g. a lubricant can be omitted when preparing a solid dosage form, especially if it comprises magnesium aluminosilicate and/or magnesium aluminometasilicate.

In a further aspect, the invention relates to the use of magnesium aluminosilicate and/or magnesium aluminometasilicate as a lubricant.

All details described herein for the main aspect of the invention apply *mutatis mutandi* to any other aspect of the invention.

LEGENDS TO FIGURES

FIG. 1 shows the correlation between amount of PEG 6000 sprayed onto lactose 125 mesh and mean granule size (geometric weight mean diameter) for a product temperature of 40–45° C. and 50–60 ° C., respectively. The dashed line indicates uncontrolled agglomeration at a PEG concentration of approx. 25% at a product temperature of 50–60° C. The products are unscreened.

Figure 6:
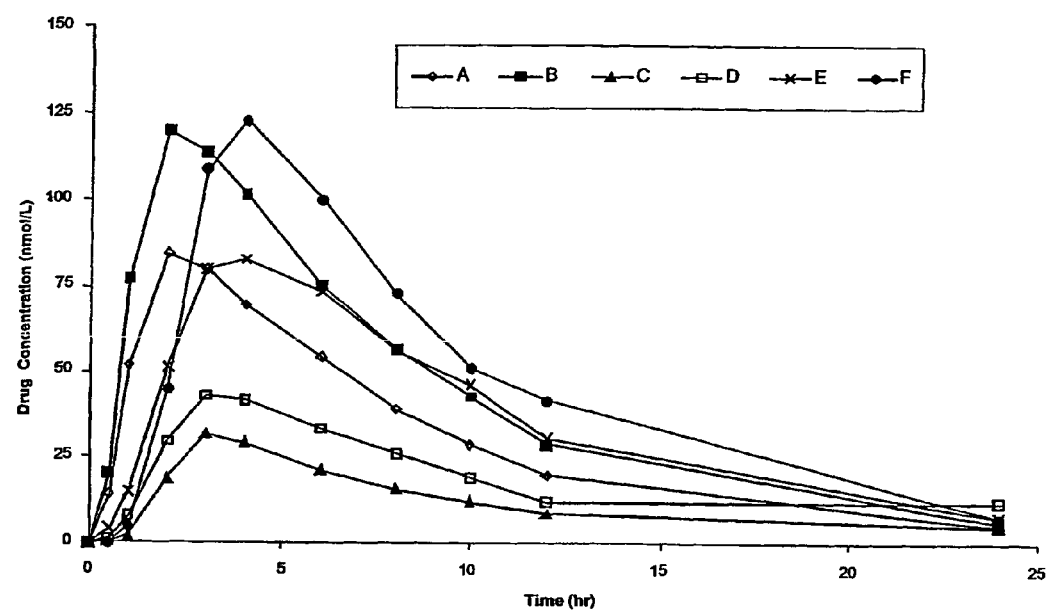

FIG. 6 shows mean serum concentrations vs. time profiles after p.o. administration of the model drug substance from Example 5 (30 mg) in six different formulations to Beagle dogs. Treatment A: 0.5% HPC (aq.), Treatment B: 5% Captisol® (aq.), Treatment C: Model drug substance from Example 5/SLS (2:1), Treatment D: Model drug substance from Example 5/SLS (1:1), Treatment E: Tween 80, Kollidon VA64, corn starch and lactose, Treatment F: Akosoft® 3103.

Figure 7:
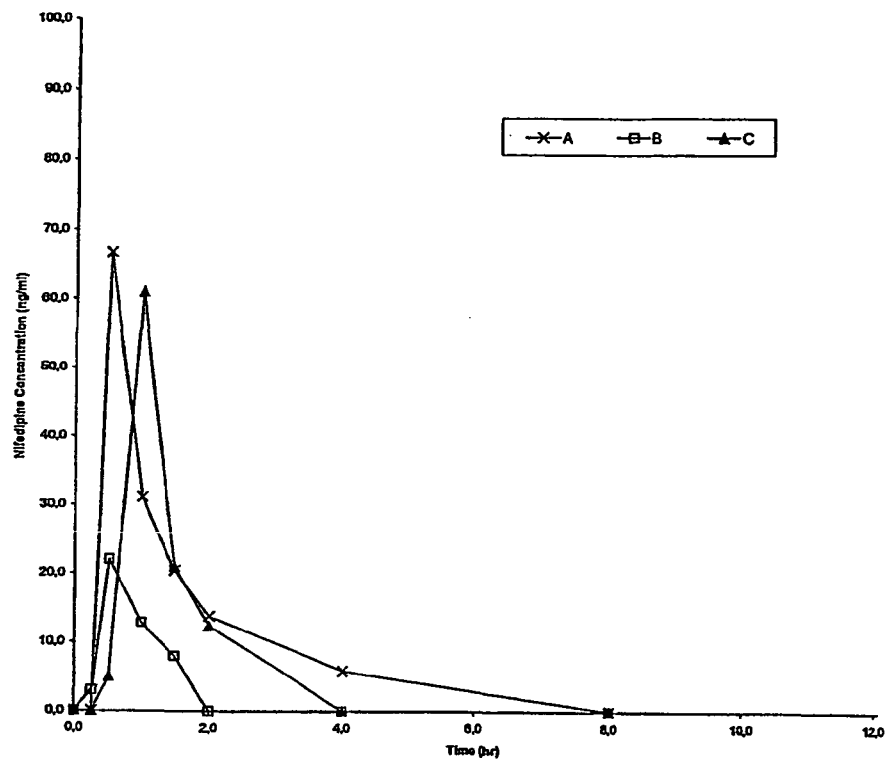

FIG. 7 shows the plasma concentration versus time curves for formulation A, B, C described in Example 6 after oral administration to dogs.

Figure 8:
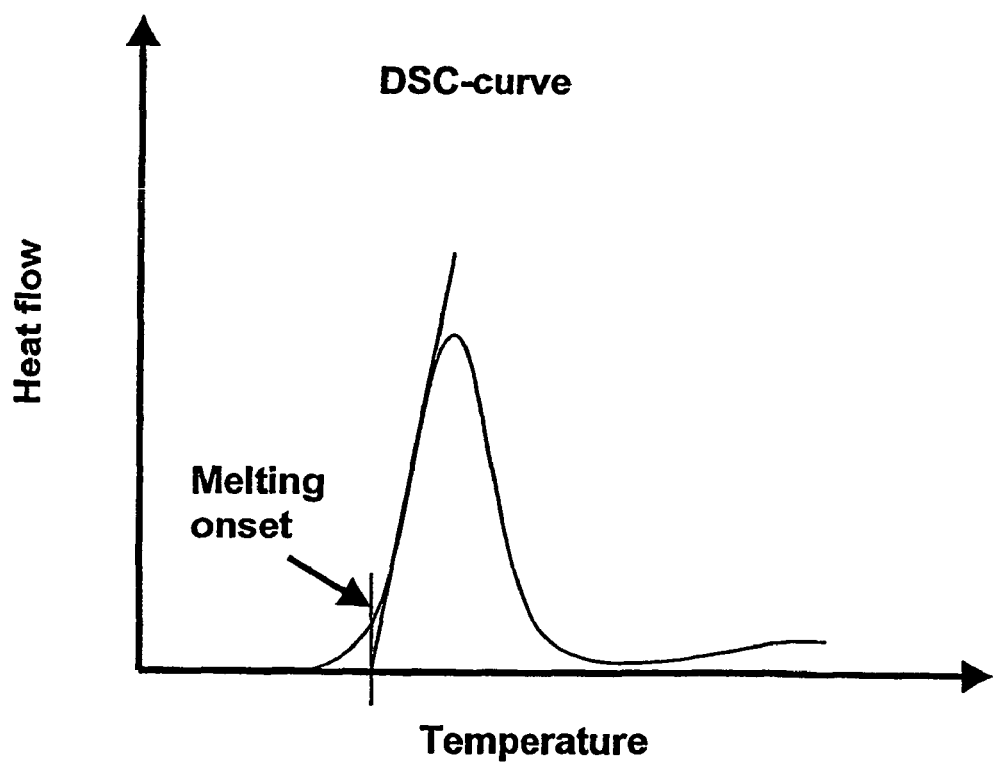

FIG. 8 illustrates determination of a melting point by a DSC curve.

The invention is further illustrated in the following examples.

Methods

Determination of Weight Variation

The tablets prepared in the Examples herein were subject to a test for weight variation performed in accordance with Ph. Eur.

Determination of Average Tablet Hardness

The tablets prepared in the Examples herein were subject to at test for tablet hardness employing Schleuniger Model 6D apparatus and performed in accordance with the general instructions for the apparatus.

Determination of Disintegration Time

The time for a tablet to disintegrate, i.e. to decompose into particles or agglomerates, was determined in accordance with Ph. Eur.

Determination of Geometric Weight Mean Diameter $d_{gw}$

The geometric weight mean diameter was determined by employment of a method of laser diffraction dispersing the particulate material obtained (or the starting material) in air. The measurements were performed at 1 bar dispersive pressure in Sympatec Helos equipment, which records the distribution of the equivalent spherical diameter. This distibution is fitted to a log normal volume-size distribution.

When used herein, "geometric weight mean diameter" means the mean diameter of the log normal volume-size distribution.

Determination of Aqueous Solubility

The aqueous solubility at 25° C. in distilled or purified water was determined by suspending a well-defined and excessive amount of the substance under investigation in a well-defined amount of distilled or purified water. The dispersion is stirred and samples are withdrawn after suitable time periods. The samples are filtered and the filtrate analysed to obtain the concentration of the substance in the sample. The concentration of the substance in the sample is then calculated according to methods well known for a person skilled in the art. The solubility is reached when the concentrations of the substance in two consecutive samples are considered identical.

Determination of Dissolution Rate

The dissolution rate was determined by employment of USP paddle dissolution method at 37° C.

Materials

All materials employed were of pharmaceutical grade.
Calcium hydrogen phosphate (Di-cafos A): Budenheim
Croscarmellose Sodium Ac-Di-Sol: FMC
Magnesium stearate: Magnesia GmbH
Polyethylene glycol: Hoechst
Lactose: DMV Other materials employed appear from the following examples.

EXAMPLES

Example 1

Preparation of Tablets Containing a Particulate Material According to the Invention The example illustrates the preparation of a particulate material comprising a relatively large amount of a carrier. The particulate material obtained exhibits good flowability, good compactability and possesses excellent tabletting properties. Thus, the particulate material allow the preparation of e.g. tablets and in spite of the relatively large load of carrier the tablets display minimal, if any, adherence (sticking) to tablet punches and/or dies during compression. Furthermore, the tablets obtained have acceptable properties with respect to disintegration, weight variation and hardness.

Starting Materials

Lactose monohydrate (DMV) 125 mesh
Calcium hydrogen phosphate anhydrous (Di-Ca-Fos P)
Polyethylene glycol 6000 (PEG 6000) having a melting point of about 60° C.

Equipment

Fluid bed Strea-1 (from Aeromatic-Fielder) mounted with a special developed top-spray binary nozzle having an opening of 0.8 mm.

Granular Compositions

| Composition 1.1 | |
| --- | --- |
| Lactose | 500 g |
| PEG 6000 | 420 g (sprayed on lactose) |

The composition has a carrier concentration of 45.6% w/w.

| Composition 1.2 | |
| --- | --- |
| Calcium hydrogen phosphate anhydrous | 500 g |
| REG 6000 | 210 g (sprayed on calcium hydrogen phosphate) |

The composition has a carrier concentration of 29.6% w/w.

Process Conditions—Description

Lactose (or for composition 1.2 calcium hydrogen phosphate anhydrous) was fluidised at appropriate inlet airflow. The inlet air was not heated. PEG 6000 was melted using an electrically heated pressure tank. The temperature was kept at a temperature at about 85° C., i.e. above the melting point of PEG 6000. The melt was pumped from the tank to the nozzle through a heated tube. In the tube, the temperature was kept at 80° C. The pressure in the tank determined the flow rate of the melt. The nozzle was heated to keep the droplets in a liquefied stage by means of heating the atomizer air delivered through the top-spray nozzle.

Settings

Inlet airflow: 30–50 $m^3$ per hour
Inlet air temperature: Ambient temperature (20–25° C.)
Tank temperature: 85° C.
Tank pressure: 1.5 Bar corresponding to a flow rate of 14–15 g/min
Tube temperature: 80° C.
Atomising air temperature: 100° C.
Process time: 28 min
Product temperature at equilibrium: 40° C. (after 15 minutes)

Product Characteristics

The products (composition 1.1 and 1.2) appear as free flowing granular products with a mean granule size of approx. 300–500 μm.

Tabletting

Compositions

| Tablet formulation I (without disintegrant) | |
| --- | --- |
| Granular product | 99% w/w |
| Magnesium stearate | 1% w/w |

The tablet formulation has a carrier concentration of 45.2% w/w.

| Tablet formulation II (with disintegrant) | |
|---|---|
| Granular product | 95% w/w |
| Ac-Di-Sol (croscarmelose sodium) | 4% w/w (disintegrant) |
| Magnesium stearate | 1% w/w |

The tablet formulation has a carrier concentration of 28% w/w.

Tablet Properties

Tablet formulation I based on composition 1.1, i.e. with lactose
  Tablet punch: Compound cup, 10 mm in diameter
  Tablet machine: Single punch machine Korsch EK0
  Tablet weight: 250 mg
  Weight variation, RSD <1%
  Average tablet hardness: 96 N
  Average disintegration time: 10 min
  Tablet appearance: White glossy tablets Tablet formulation I based on composition 1.2, i.e. with dicalcium phosphate
  Tablet punch: Compound cup, 10 mm in diameter
  Tablet machine: Single punch machine Korsch EK0
  Tablet weight: 450 mg
  Weight variation, RSD <1%
  Average tablet hardness: 121 N
  Average disintegration time: 17 min
  Tablet appearance: White glossy tablets Tablet formulation II based on composition 1.1, i.e. with lactose
  Tablet punch: Compound cup, 10 mm in diameter
  Tablet machine: Single punch machine Korsch EK0
  Tablet weight: 250 mg
  Weight variation, RSD <1%
  Average tablet hardness: 112 N
  Average disintegration time: 8 min
  Tablet appearance: White glossy tablets Thus, addition of a disintegrant results in a decrease in the average disintegration time without any other changes of importance.

Tablet formulation II based on composition 1.2, i.e. with calcium hydrogen phosphate
  Tablet punch: Compound cup, 10 mm in diameter
  Tablet machine: Single punch machine Korsch EK0
  Tablet weight: 450 mg
  Weight variation, RSD <1%
  Average tablet hardness: 118 N
  Average disintegration time: 9 min
  Tablet appearance: White glossy tablets When calcium dihydrogen phosphate anhydrous is employed a more pronounced decrease in disintegration time is observed compared with that of lactose. The average tablet hardness is maintained at an excellent level.

Example 2

Controlled Agglomeration—Proof of Concept

Method

Controlled agglomeration is obtained by keeping the product temperature at minimum 10° C. below melting point of the carrier reducing the probability of agglomeration due to coalescence. Controlled agglomeration is characterised by gradual increase in mean granule size (geometric weight mean diameter $d_{gw}$) as function of applied amount of carrier. In contrast, uncontrolled agglomeration shows rapidly increasing granule size. As a proof of concept the granule growth pattern are compared corresponding to the following conditions:

Inlet fluidising air temperature of ambient temperature: 20–25° C.
  Inlet fluidising air temperature of 85° C. leading to a temperature of the product of about 50–60° C., Starting Materials
  Lactose monohydrate 125 mesh
  Polyethylene glycol 6000

Equipment
  Fluid bed Strea-1 mounted with a top-spray binary nozzle.

Granular Compositions

| | |
|---|---|
| Lactose | 400 g |
| PEG 6000 | Increased stepwise in separate experiments (from 0% to about 60% w/w in the final composition) |

Process Conditions

The conditions were the same as described in Example 1.

Settings (Controlled Agglomeration)
  Inlet airflow: 30–50 m³ per hour
  Inlet air temperature: Ambient temperature (20–25° C.)
  Tank temperature: 90° C.
  Tank pressure: 1.5 Bar corresponding to a flow rate of 14–15 g/min
  Tube temperature: 85° C.
  Atomizer air temperature: 100° C.
  Product temperature at equilibrium: 40° C.

Settings (Uncontrolled Agglomeration)
  Inlet airflow: 30–50 m³ per hour
  Inlet air temperature: 85° C.
  Tank temperature: 90° C.
  Tank pressure: 1.5 Bar corresponding to a flow rate of 14–15 g/min
  Tube temperature: 85° C.
  Atomizer air temperature: 100° C.
  Product temperature at equilibrium: 55–65° C.

Product Characteristics

Figure 1:
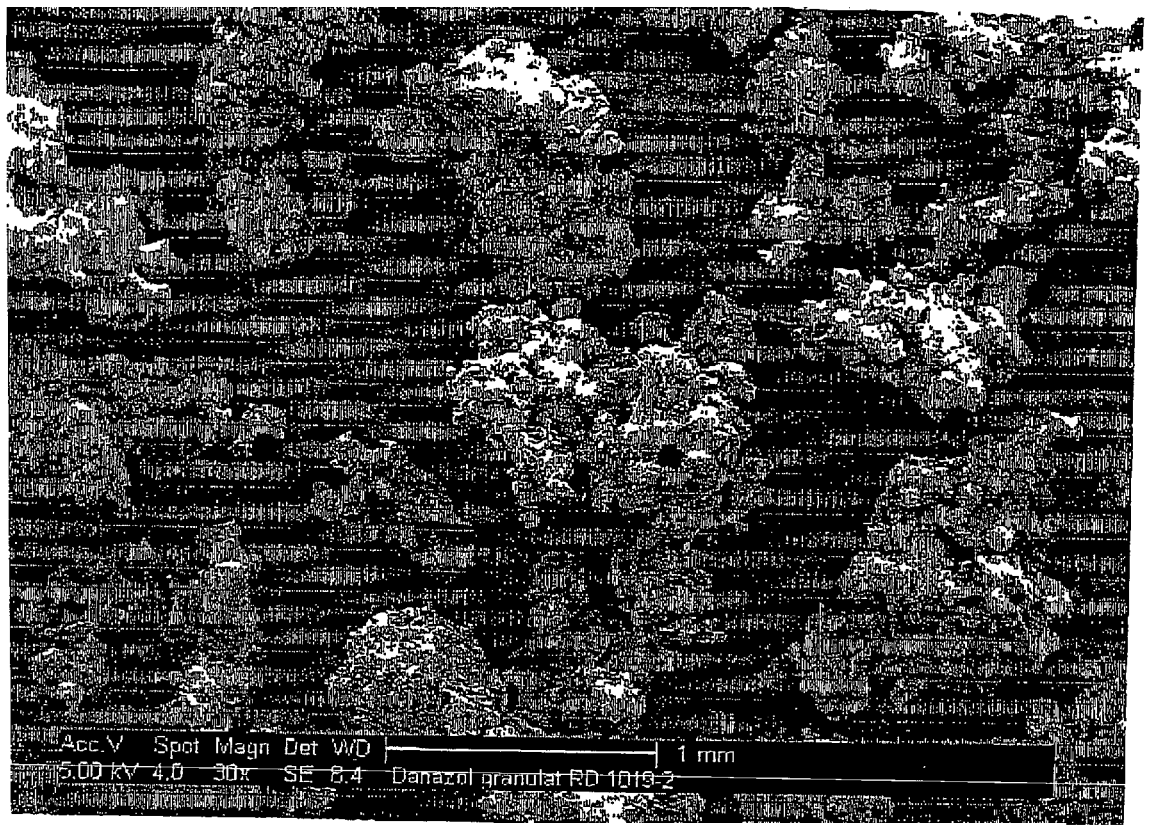
Figure 2:
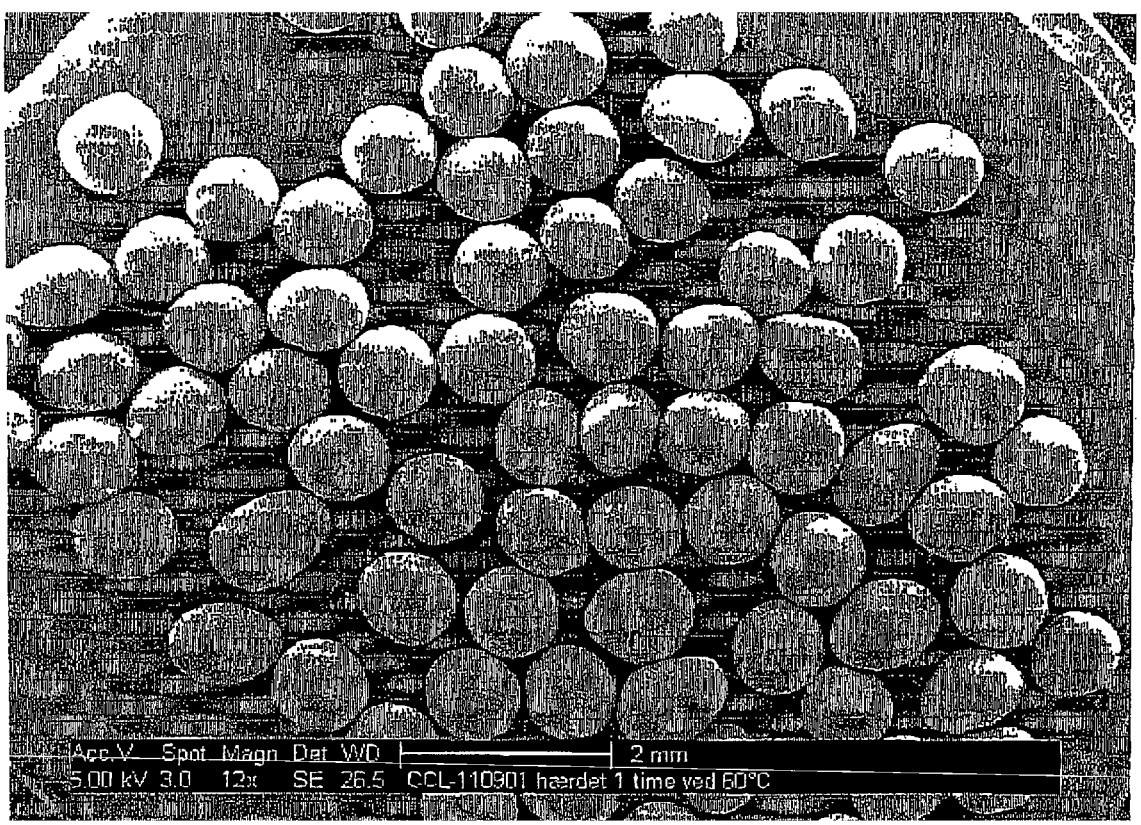
FIG. 2 shows the relationship between obtainable dose and drug solubility in a carrier at different concentrations of carrier assuming a formulation unit weight of 500 mg.
Figure 3:
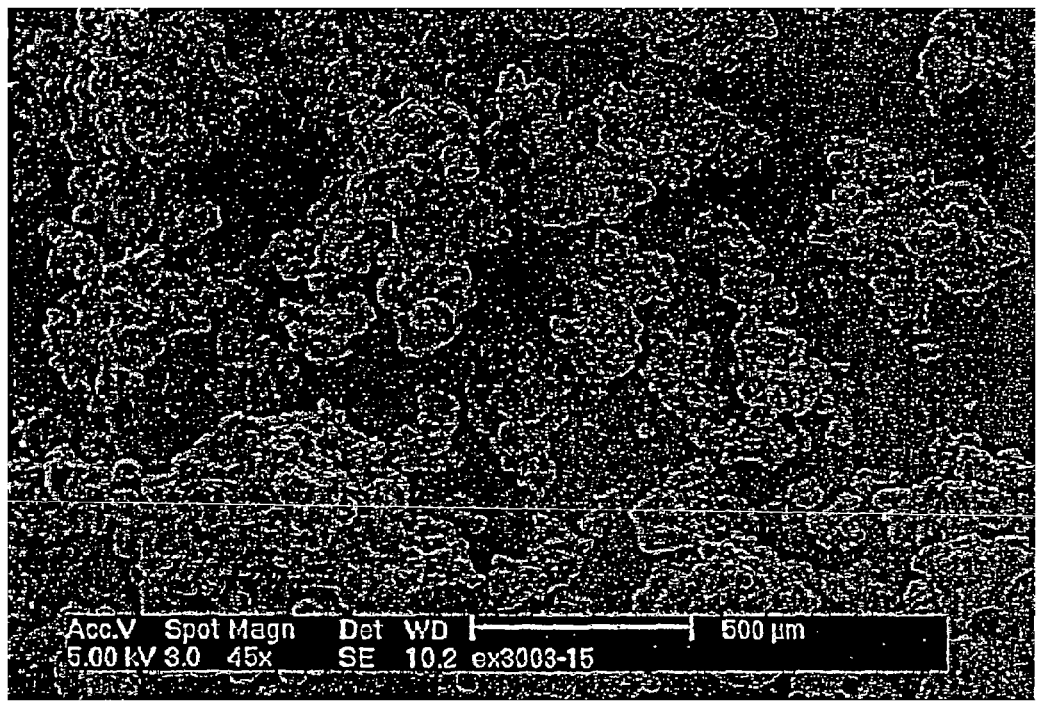
FIG. 3 is a SEM micrograph of PEG sprayed onto lactose 125 mesh; the PEG concentration is 48% w/w. Magnification×45.
Figure 4:
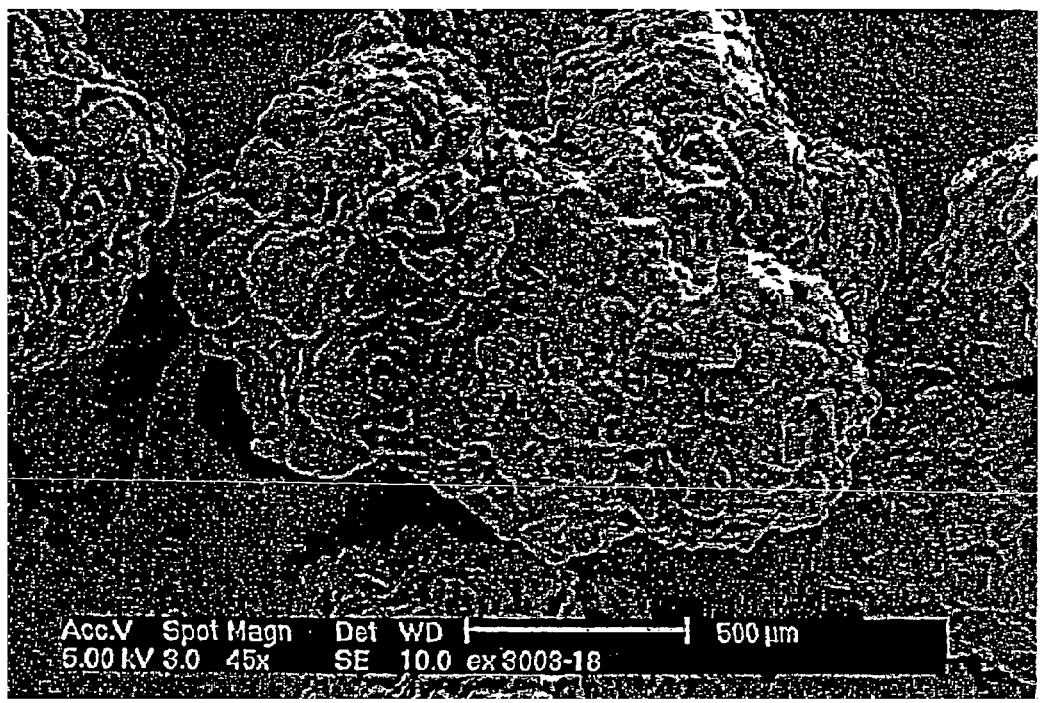
FIG. 4 is a SEM micrograph of PEG sprayed onto lactose 125 mesh; the PEG concentration is 25% w/w. Magnification×45.

Increasing amounts of PEG were sprayed onto the fluidised lactose particles and the particle size distribution of the products was analysed by method of laser diffraction, dispersing the agglomerates in air. The correlation between mean granule size (geometric weight mean diameter $d_{gw}$) and applied amount of carrier demonstrates the difference between controlled and uncontrolled agglomeration as shown in FIG. 1 and Table 1. Table 1 includes the geometric standard deviation $s_g$ related to the wideness of the size distribution.

TABLE 1

Particle size characteristics of granulate products produced by agglomeration by melt spraying in fluid bed at heated and unheated inlet air conditions at different applied amount of PEG 6000 concentrations.

| Product temperature 40–45° C. Inlet air temperature: Ambient | | | Product temperature 50–60° C. Inlet air temperature: 85° C. | | |
|---|---|---|---|---|---|
| PEG, w/w % | $D_{gw}$, μm | $S_g$ | PEG w/w % | $D_{gw}$, μm | $S_g$ |
| 0 | 55 | 2.37 | 0 | 55 | 2.37 |
| 17 | 151 | 2.09 | 13 | 343 | 1.98 |
| 26 | 261 | 2.09 | 15 | 513 | 1.48 |
| 38 | 328 | 2.06 | 25 | 980 | 1.43 |
| 48 | 332 | 1.95 | | | |
| 60 | 450 | 1.8 | | | |

$D_{gw}$: Geometric weight mean diameter.
$S_g$: Geometric standard deviation.

Example 3

Improving tabletting Characteristics of Paracetamol Applying the controlled Agglomeration Technique Parcetamol has been chosen as model substance representing a substance with poor compression characteristics. By incorporation of PEG 6000 by melt spraying, i.e. spraying melted PEG 6000 on paracetamol, a granular product of paracetamol is obtained with excellent flowability and tablet compression characteristics. In order to obtain tablets with satisfactory disintegration time Avicel PH 200 and Kollidon CL (super-disintegrant) has been added to the product Starting Materials
  Polyethyleneglycol 6000 (Hoechst)
  Paracetamol (Unikem)

Equipment
  Fluid bed Strea-1 (Aeromatic-Fielder)

Process Conditions
  300 g PEG 6000 was melted by heating to 90° C. in a pressure tank. The melted carrier was pumped through a heated tube (85° C.) to the binary nozzle in the fluid bed at a tank pressure of 1.5 Bar. The atomizing air was heated to 140° C. The inlet air temperature of the fluid bed was 25° C.
  241 g of PEG was sprayed on 250 fluidized paracetamol at a flow rate of 17 g/min. The total yield was 491 g granulate with a composition corresponding to 49,1% w/w PEG 6000 and 50.9% w/w paracetamol. The maximum product temperature was 36° C. at the end of the process.

Product Characteristics
  The median particle size on volume basis is 85 μm for paracetamol was increased to 295 μm during the controlled agglomeration process. The median particle size was determined by laser diffraction (Helos) dispersing the particles in air.

| Tablet composition | |
|---|---|
| Paracetamol | 44% |
| PEG 6000 | 41% |
| Avicel PH200 | 10% |
| Kollidon CL | 4% |
| Magnesium stearate | 1% |

Paracetamol and PEG 6000 are employed in the form of the granular product obtained as described above.
Avicel PH is blended with the granular product for 2 minutes in Turbula mixer and after adding magnesium stearate for further 0.5 minutes. Avicel PH200 (microcrystalline cellulose) is supplied by FMC, Kollidon CL by BASF and magnesium stearate by Magnesia GmbH.

Tabletting and Tablet Characteristics
  The tabletting was performed on a single punch tabletting machine Korsch EK0
  Tablet shape 8 mm doomed shape
  Weight: 200 mg
  Strength 87 mg
  Mean tablet hardness (n=10) determined on a Schleuninger Model 6D apparatus was 77 N
  Friability was 0.2% determined at a Roche friabililator
  Mean disintegration time was 11 minutes (Ph.Eur)
  Weight variation (n=20) corresponded to RSD of 0.6%

In conclusion, the tablets obtained from the granulate prepared by the controlled agglomeration method of the invention were very satisfactory and only a relatively small concentration of tabletting excipients was needed in order to ensure a suitable tabletting process. Furthermore, the example demonstrates that it is possible to obtain a granulate that has a relatively high concentration of carrier (about 50% w/w) and at the same time has a suitable particle size for further processing.

Example 4

In Vivo Bioavailability in Dogs After Administration of Tablets Containing a Particulate Material Obtained by the Controlled Agglomeration Method of the Present Invention—Proof of Concept The present example illustrates that a composition containing a particulate material obtained according to the present invention leads to improved bioavailability after oral administration to dogs compared with compositions made by techniques that are generally accepted as useful when an increase in bioavailability is desired. In the present example compositions in the form of a nanosuspension and a microemulsion are used for comparison.

The model drug substance employed illustrates a drug substance that has a very low aqueous solubility of less than 50 ng/ml independent on pH. The molecular weight of the model drug substance is about 600 and it has a lipophilicity i.e. a log P (octanol/water) of 5.0.

Proof of concept is based on a comparison of bioavailability of different oral formulations and an I.V. injection of the drug substance in dogs (n=4). Data on the I.V. is not included in this example.

Treatment Compositions and Treatment Schedule
  Treatment A (comparison treatment): nanosuspension containing 2% w/w of the model drug substance. NanoCrystal™ colloidal suspension of the model drug substance stabilised with hydroxy propyl cellulose (HPC-SL). Supplier: Élan pharmaceutical technologies, USA. EPT Ref.

NB: GOT-5747-170. The nanosuspension contains 2% of the model drug substance and 1% HPC-SL (w/w). A treatment consisted in oral administration of 36.3 mg as a sigle dose (approximately 1.8 ml).

Treatment B (according to the invention): tablets containing a particulate material obtained according to the method of the present invention. The tablets contain about 1% w/w of the model drug substance. The preparation of the composition used in Treatment B is described below. A treatment consisted in oral administration of 6 tablets as a single dose corresponding to approx. 37.5 mg.

Treatment C (according to the invention): tablets containing a particulate material obtained according to the method of the present invention. The tablets contain about 5% w/w of the model drug substance. The preparation of the composition used in Treatment C is described below. A treatment consisted in oral administration of 2 tablets as a single dose corresponding to approx. 42.4 mg.

Treatment D (comparison treatment): capsules containing a microemulsion of the model drug substance. Soft gelatine capsules containing 7.3 mg of the model drug substance in a vehicle consisting of 40% w/w Softigen 767, 15% w/w trietylcitrate and 45% w/w polysorbate 80 (0.05% BHA was added by weight as antioxidant). A treatment consisted of a single dose of 5 capsules, equivalent to 36.5 mg of the model drug substance.

Treatment E (comparison treatment): capsules containing a microemulsion of the model drug substance. Soft gelatine capsules containing 12.43 mg of the model drug substance in a vehicle consisting of 40% w/w Softigen 767, 15% w/w trietylcitrate and 45% w/w polysorbate 80 (0.05% BHA was added by weight as antioxidant). A treatment consisted of a single dose of 3 capsules, equivalent to 37.2 mg of the model drug substance.

Preparation of a Pharmaceutical Composition According to the Invention used in Treatment B (5 mg Model Drug Substance)

Preparation of a Particulate Material—Melt-spraying Process

Starting Materials
 Polyethyleneglycol 6000 (Hoechst)
 Poloxamer 188 (BASF)
 Model drug substance
 Avicel PH 101 (FMC)

Equipment
 Fluid bed Strea-1 (Aeromatic-Fielder)

Process Conditions 198.0 g PEG 6000 and 85.0 g Poloxamer 188 (70:30 w/w) were melted by heating to 75° C. in a pressure tank. 6.21 g model drug substance was dissolved in the melted carriers. The melt was pumped through a heated tube (80° C.) to the binary nozzle in the fluid bed at a tank pressure of 1.8 Bar. The atomizing air was heated to 140° C. The inlet air temperature of the fluid bed was 22° C.

289 g of melt was sprayed on 300 g fluidized Avicel PH 101 at a flow rate of 10 g/min. The total yield was 589 g granulate. The maximum product temperature was 36° C. at the end of the process.

Product Characteristic

Granular, free flowing product with a particle size under 0.7 mm.

Tablet Composition (w/w)

Tablets were obtained by compression of a powder blend containing the granulate obtained as described above with magnesium stearate.

| Model drug substance | 1.04% |
| PEG 6000 | 33.26% |
| Poloxamer 188 | 14.29% |
| Avicel PH101 | 50.41% |
| Magnesium stearate | 1.00% |

Magnesium stearate was blended with the granulate for 0.5 minutes in a Turbula-mixer.

Tabletting and Tablet Characteristics

The tabletting was performed on a single punch tabletting machine Korsch EK0

Tablet shape 11.5 mm doomed shape

Weight: 515 mg

Strength 5 mg

Mean tablet hardness (n=10) determined on a Schleuninger Model 6D apparatus was 105 N Mean disintegration time was 21.5 minutes (Ph.Eur)

Weight variation (n=20) corresponded to RSD of 0.9%

Preparation of a Pharmaceutical Composition According to the Invention used in Treatment C (20 mg Model Drug Substance)

Preparation of a Particulate Material—Melt-spraying Process

Starting Materials
 Polyethyleneglycol 6000 (Hoechst)
 Poloxamer 188 (BASF)
 Model drug substance
 Avicel PH 101 (FMC)

Equipment
 Fluid bed Strea-1 (Aeromatic-Fielder)

Process Conditions 121.9 g PEG 6000 and 52.3 g Poloxamer 188 (70:30 w/w) were melted by heating to 75° C. in a pressure tank. 20.96 g model drug substance was dissolved in the melted carriers. The melt was pumped through a heated tube (80° C.) to the binary nozzle in the fluid bed at a tank pressure of 1.8 Bar. The atomizing air was heated to 140° C. The inlet air temperature of the fluid bed was 22° C.

195 g of melt was sprayed on 200 g fluidized Avicel PH 101 at a flow rate of 11.4 g/min. The total yield was 395 g granulate. The maximum product temperature was 37° C. at the end of the process.

Product Characteristic

Granular, free flowing product with a particle size under 0.7 mm.

Tablet Composition (w/w)

Tablets were obtained by compression of a powder blend containing the granulate obtained as described above with magnesium stearate.

| | |
|---|---|
| Model drug substance | 5.26% |
| PEG 6000 | 30.54% |
| Poloxamer 188 | 13.11% |
| Avicel PH101 | 50.09% |
| Magnesium stearate | 1.00% |

Magnesium stearate was blended with the granulate for 0.5 minutes in a Turbula-mixer.

Tabletting and Tablet Characteristics

The tabletting was performed on a single punch tabletting machine Korsch EK0
Tablet shape 11.5 mm doomed shape
Weight: 409 mg
Strength 20 mg
Mean tablet hardness (n=10) determined on Schleuninger Model 6D apparatus was 41 N
Mean disintegration time was 5.5 minutes (Ph.Eur)
Weight variation (n=20) corresponded to RSD of 1.3%

Study Design and Results

The study design was a cross-over study, which comprised all four dogs in one group. In each of totally six weeks the dogs were dosed orally on the first day of the week following by 6 days of recovery. The first week the dogs were assigned to treatment A, second week to treatment B etc.

Summary of pharmacokinetic parameters. Beagle dogs after single oral dosing of the model drug substance (±SD, n=4).

administration to dogs compared with compositions made by techniques that are generally accepted as useful when an increase in bioavailability is desired. In the present example compositions in the form of a nanosuspension and a cyclodextrin solution are used for comparison.

The model drug substance employed illustrates a drug substance that has a very low aqueous solubility of about 50 pg/ml in phosphate buffer pH 7.4. The model drug substance in this example has a $pK_A$ of 8, a molecular weight of about 450 and a lipophilicity i.e. a log P (octanol/buffer pH 7.4) of 6.0. The model drug substance is employed in the form of a hydrochloride salt. The aqueous solubility of the salt is also very low.

The results presented below are based on absorption study in dogs comparing 6 different formulations.
Formulation A (nanosuspension)
Formulation B: Cyclodextrin solution (Captisol)
Formulation C: Mixture of SLS and the model drug substance (0.5:1)
Formulation D: Mixture of SLS and the model drug substance (1:1)
Formulation E: Granulate with 10% Tween 80
Formulation F: (granulate in capsule) prepared by a method according to the present invention by melt spraying and using Akosoft XP 3103.

A summary of the pharmacokinetic report on the study is given below.

Test formulation A was prepared by suspending nanonised model drug substance particles in a vehicle of 0.5% HPC (HPC) (Klucel® MF EP, Hercules Inc.) and purified water.

| Treatment | A | B | C | D | E |
|---|---|---|---|---|---|
| $t_{max}$ (h) | 2.2 ± 0.5 | 2.8 ± 0.5 | 4.3 ± 3.2 | 2.8 ± 1.3 | 2.0 ± 0.0 |
| $C_{max}$ (ng/ml) | 19 ± 8 | 52 ± 15 | 29 ± 17 | 35 ± 13 | 42 ± 6 |
| $AUC_{0-inf}$[a] (ng/ml) | 206 ± 108 | 489 ± 187 | 290 ± 184 | 318 ± 144 | 318 ± 65 |
| F[b] (%) | 4.8 ± 1.9 | 11 ± 4 | 5.4 ± 2.7 | 7.8 ± 3.8 | 7.6 ± 2.9 |

Figure 5:
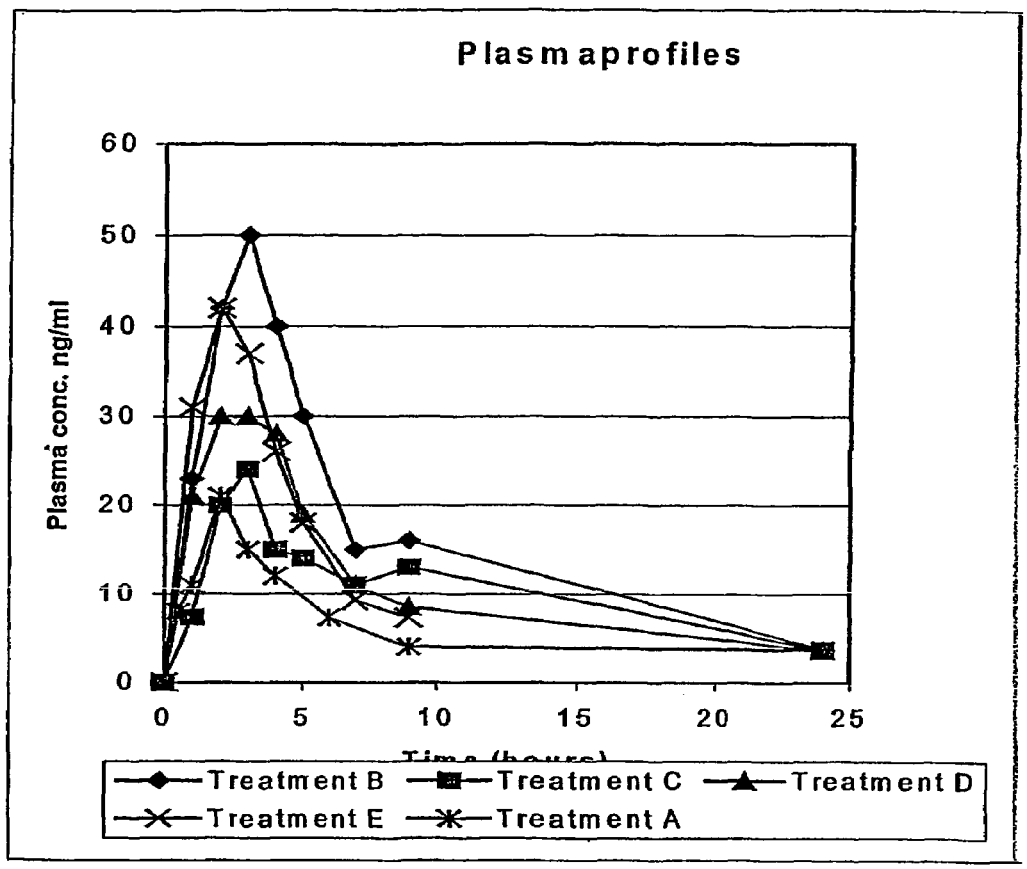
FIG. 5 shows results from Example 4.

Calculated as
[a] $AUC_{last} + C_{last}*t_{1/2,i.v.}/\ln 2$;
[b] $AUC_{0-inf,po} \cdot D_{iv}/(AUC_{0-inf,iv} \cdot D_{po})$ From the results given above it and in FIG. 5 is seen that treatment B leads to improved bioavailability compared with all other treatments employed. It is particularly interesting to note that compositions containing the model drug substance in dissolved form (treatment D and E) do not lead to a better bioavailability than treatment B and there is no significant difference in the $t_{max}$ values obtained, i.e. the onset of the therapeutic effect is the same even if a solid composition is used. Treatment C leads to a lower bioavailability than treatment B, which may be explained by the fact that the ration between the amount of drug substance in the carrier is higher in treatment C than in treatment B (higher dose in treatment C than in treatment B).

Example 5

In Vivo Bioavailability in Dogs After Administration of Tablets Containing a Particulate Material Obtained by the Controlled Agglomeration Method of the Present Invention—Proof of Concept II The present example illustrates that a composition containing a particulate material obtained according to the present invention leads to improved bioavailability after oral A similar suspension was included in an initial study where it resulted in a mean relative bioavailability of only 0.64 when compared to a 5% Captisol® solution. However, it was suspected that the initial suspension used was not optimal, as the particle size distribution was above the micrometer range. Subsequently, the micronisation process has been optimised, and test formulation A was prepared from a model drug substance batch, which contained particles in the nanometer range.

Reference formulation B was prepared by dissolving the model drug substance in an aqueous vehicle of 5% β-cyclodextrin sulfobutyl ether, sodium salt (Captisol®, CyDex Inc).

Test formulation C was prepared by dissolving sodium lauryl sulphate (SLS) in water and adding the solution to the model drug substance drop by drop (model drug substance/SLS w/w-ratio 2:1). The dried mixture and lactose were filled in capsules.

Test formulation D was prepared by dissolving SLS in water and adding the solution to the model drug substance drop by drop (model drug substance/SLS w/w-ratio 1:1). The dried mixture and lactose were filled in capsules.

Test formulation E was prepared by melt granulation of the model drug substance, 10% Tween 80, 2% Kollidon VA64, corn starch and lactose. The granulate was filled in capsules.

Test formulation F was prepared by a method of the invention by melt spraying the model drug substance, Akosoft 3103 and lactose. The granulate obtained was filled in capsules. Akosoft 3103 is a mixture of Akoline HH ($C_8$–$C_{10}$ monoglycerides), Akosoft 36 (hydrogenated cocoglyceride) and Akofine NF (hydrogenated cottonseed oil) from Karlshamns AB. All are saturated fats or oils, i.e. no double-bonds, PEG-chains or free acid groups exist in the excipients.

In the following the preparation of test formulation F is described in further details.

Test Formulation F

Preparation of a Particulate Material—Melt-spraying Process

Starting Materials
  Akosoft XP 3103 (Karlshamn)
  Model drug substance
  Lactose 350 M (DMV)

Equipment
  Fluid bed Strea-1 (Aeromatic-Fielder)

Process Conditions 153 g Akosoft XP 3103 was melted by heating to 70° C. in a pressure tank. The melt was pumped through a heated tube (80° C.) to the binary nozzle in the fluid bed at a tank pressure of 0.3 Bar. The atomizing air was heated to 140° C. The inlet air temperature of the fluid bed was 22° C.

114 g of melt was sprayed on fluidized material consisting of 256.5 g lactose 350 M and 43.5 g model drug substance at a flow rate of 30 g/min. The total yield was 414 g granulate. The maximum product temperature was 32° C. at the end of the process.

Product Characteristic
  Granular product with a particle size under 0.7 mm.
  The product was filled into capsules (500 mg corresponding to 30 mg base)

Study Design and Dosing

The study was conducted in a cross-over design. After a five days pre-dose period the test formulations were administered in intervals of three or four days. Test formulations were administered in the order B, A, C, D, E and F.

On days of dosing each dog was dosed in the morning with 30 mg of the model drug substance (with regard to the base) irrespective of bodyweight. The dose level chosen was based on previous studies with the model drug substance in Beagle dogs.

Pharmacokinetic Results

Mean serum concentrations vs. time are presented in FIG. 6. Standard deviations are omitted in the figure for clarity. The data is shown in the Table below The concentration of the model drug substance in the serum sample taken from dog F1131 at 24 hours is high compared to the concentrations observed at previous time points. Re-analysis confirmed the result and the late serum concentration increase might therefore be due to delayed absorption of the test compound.

Pharmacokinetic parameters for the model drug substance estimated by standard non-compartmental analysis are given in the following Table.

For the reference solution a mean $t_{max}$ of 2.5 hours was observed. The other treatments resulted in mean $t_{max}$ values of 2.3 hours (HPC—formulation A), 3.0 hours (model drug substance/SLS 2:1—formulation C), 3.8 hours (Akosoft 3103—formulation F), 4.8 hours (Tween 80/Kollidon VA64—formulation E) and 8.3 hours (model drug substance/SLS 1:1—formulation D). The latter mean $t_{max}$ value is high due to the extreme contribution from dog F1131 (see above). If this data point is omitted a mean $t_{max}$ of 3.0 hours is observed.

With a mean maximum serum concentration at 123 nmol·$L^{-1}$ the Akosoft 3103 formulation (formulaion F) gave a value almost similar to the reference solution at 124 nmol·$L^{-1}$. At the other extreme the treatments with SLS (formulations C and D) resulted in mean $C_{max}$ values of 31.5 nmol·$L^{-1}$ (model drug substance/SLS 2:1) and 50.3 nmol·$L^{-1}$ (model drug substance/SLS 1:1). Again the mean value would be smaller if the 24 hours data point for formulation D was omitted. Administration of the HPC- and Tween 80/Kollidon VA64-formulations resulted in mean $C_{max}$ values of 87.9 nmol·$L^{-1}$ and 85.3 nmol·$L^{-1}$, respectively.

In the Table on next page are given individual and mean (n=4) pharmacokinetic parameters of the model drug substance employed in Example 5 after dosing of 30 mg to Beagle dogs. Treatment A: 0.5% HPC (aq.), Treatment B: 5% Captisol® (aq.), Treatment C: model drug substance/SLS (2:1), Treatment D: model drug substance/SLS (1:1), Treatment E: Tween 80, Kollidon VA64, corn starch and lactose, Treatment F: Akosoft® 3103.

| Treatment[a] | Animal | Dose[b] (nmol/kg) | $t_{max}$ (h) | $C_{max}$ (nmol·$L^{-1}$) | $AUC_{0-t}$ (nmol·h·$L^{-1}$) | $AUC_{0-inf}$ (nmol·h·$L^{-1}$) | $AUC_{\%residual}$ | $t_{1/2}$[c] (h) | CL/F (L·$kg^{-1}$·$h^{-1}$) | $V_2/F$ (L·$kg^{-1}$) | $F_{rol,Inf}$[d] | $F_{rol,t}$[e] |
|---|---|---|---|---|---|---|---|---|---|---|---|---|
| A | F1131 | 4381 | 2.0 | 82.3 | 617 | 657 | 6.1 | 3.9 | 6.67 | 37.6 | 0.58 | 0.57 |
|   | F1132 | 4440 | 2.0 | 61.3 | 407 | 418 | 2.7 | 4.3 | 10.6 | 66.2 | 0.52 | 0.52 |
|   | F1138 | 4595 | 3.0 | 109 | 1025 | 1067 | 4.0 | 4.9 | 4.31 | 30.6 | 0.95 | 0.94 |
|   | F1139 | 5016 | 2.0 | 99.0 | 751 | 780 | 3.7 | 4.7 | 6.40 | 44.0 | 1.04 | 1.04 |
|   | Mean |  | 2.3 | 87.9 | 700 | 731 | 4.1 | 4.5 | 7.0 | 44.6 | 0.77 | 0.77 |
|   | CV % |  | 21.7 | 23.7 | 37.0 | 36.9 | 34.9 | 9.85 | 37.5 | 34.5 | 33.9 | 33.9 |
| B (reference) | F1131 | 4730 | 3.0 | 145 | 1163 | 1231 | 5.5 | 5.3 | 3.84 | 29.6 | — | — |
|   | F1132 | 4794 | 3.0 | 101 | 842 | 873 | 3.5 | 4.7 | 5.49 | 37.2 | — | — |
|   | F1138 | 4995 | 2.0 | 141 | 1180 | 1217 | 3.0 | 4.7 | 4.11 | 27.6 | — | — |
|   | F1139 | 5560 | 2.0 | 107 | 804 | 832 | 3.4 | 4.7 | 6.71 | 45.4 | — | — |
|   | Mean |  | 2.5 | 124 | 997 | 1038 | 3.9 | 4.9 | 5.0 | 35.0 | — | — |
|   | CV % |  | 23 | 18 | 20 | 21 | 29 | 6.1 | 27 | 23 | — | — |

-continued

| Treatment[a] | Animal | Dose[b] (nmol/kg) | $t_{max}$ (h) | $C_{max}$ (nmol · $L^{-1}$) | $AUC_{0-t}$ (nmol · h · $L^{-1}$) | $AUC_{0-inf}$ (nmol · h · $L^{-1}$) | $AUC_{\%residual}$ | $t_{1/2}$[c] (h) | CL/F (L · $kg^{-1}$ · $h^{-1}$) | $V_z$/F (L · $kg^{-1}$) | $F_{rel,Inf}$[d] | $F_{rol,t}$[e] |
|---|---|---|---|---|---|---|---|---|---|---|---|---|
| C | F1131 | 4762 | 3.0 | 12.5 | 78 | 95 | 17 | 4.1 | 50.2 | 297 | 0.08 | 0.07 |
|   | F1132 | 4794 | 3.0 | 8.63 | 53 | 66 | 20 | 4.3 | 73.0 | 455 | 0.08 | 0.06 |
|   | F1138 | 5030 | 3.0 | 6.86 | 51 | 73 | 30 | 6.1 | 69.3 | 608 | 0.06 | 0.04 |
|   | F1139 | 5580 | 3.0 | 98.0 | 781 | 817 | 4.4 | 4.9 | 8.83 | 48.2 | 0.98 | 0.97 |
|   | Mean |  | 3.0 | 31.5 | 241 | 263 | 17.9 | 4.9 | 50 | 352.1 | 0.30 | 0.29 |
|   | CV % |  | 0.0 | 141 | 150 | 141 | 58.9 | 18.4 | 61.0 | 67.9 | 151 | 158 |
| D | F1131 | 4730 | 24 | 32.5 | 321 | 610 | 47 | 6.2 | 7.75 | 68.9 | 0.11 | 0.28 |
|   | F1132 | 4826 | 2.0 | 34.1 | 291 | 339 | 14 | 4.7 | 14.2 | 96.1 | 0.27 | 0.23 |
|   | F1138 | 4995 | 3.0 | 27.7 | 236 | 249 | 5.1 | 5.2 | 20.0 | 150 | 0.20 | 0.20 |
|   | F1139 | 5537 | 4.0 | 107 | 913 | 957 | 4.6 | 4.9 | 5.80 | 41.1 | 1.16 | 1.14 |
|   | Mean |  | 8.3 | 50.3 | 440 | 539 | 17.7 | 5.3 | 12 | 89.0 | 0.44 | 0.46 |
|   | CV % |  | 127 | 75.3 | 72.1 | 59.0 | 113 | 12.6 | 54.3 | 52.2 | 111 | 98.5 |
| E | F1131 | 4826 | 6.0 | 43.2 | 575 | 752 | 24 | 10 | 8.42 | 95.4 | 0.60 | 0.48 |
|   | F1132 | 4859 | 6.0 | 78.8 | 802 | 835 | 4.0 | 4.5 | 5.82 | 38.1 | 0.94 | 0.94 |
|   | F1138 | 5030 | 3.0 | 102 | 956 | 1015 | 5.8 | 5.5 | 4.95 | 39.0 | 0.83 | 0.80 |
|   | F1139 | 5537 | 4.0 | 117 | 1058 | 1118 | 5.3 | 6.2 | 5.00 | 37.4 | 1.35 | 1.33 |
|   | Mean |  | 4.8 | 85.3 | 848 | 930 | 9.8 | 6.3 | 5.5 | 52.5 | 0.93 | 0.89 |
|   | CV % |  | 31.3 | 37.7 | 24.8 | 17.9 | 97.1 | 39.7 | 12.8 | 54.5 | 33.7 | 39.6 |
| F | F1131 | 4762 | 3.0 | 152 | 1334 | 1414 | 5.7 | 5.3 | 3.37 | 25.6 | 1.14 | 1.14 |
|   | F1132 | 4826 | 4.0 | 99.1 | 839 | 867 | 3.3 | 4.4 | 5.56 | 35.1 | 0.99 | 0.99 |
|   | F1138 | 5102 | 4.0 | 88.1 | 881 | 926 | 4.8 | 5.0 | 5.51 | 40.1 | 0.74 | 0.73 |
|   | F1139 | 5537 | 4.0 | 153 | 1210 | 1266 | 4.4 | 4.8 | 4.37 | 30.1 | 1.53 | 1.52 |
|   | Mean |  | 3.8 | 123 | 1066 | 1118 | 4.6 | 4.9 | 4.7 | 32.7 | 1.10 | 1.10 |
|   | CV % |  | 13.2 | 27.9 | 22.9 | 23.6 | 21.6 | 7.70 | 22.2 | 19.2 | 30.0 | 31.0 |

Individual doses used in the pharmacokinetic analysis were calculated by $D \cdot CF/M_w \cdot BW$; D is the dose administered with respect to the base (ng), $M_w$ is the molecular weight of the base (ng/nmol), BW is the body weight of the animal (kg) and CF is the correction factor determined from analysis of the test formulations.

$t_{1/2}$ was calculated from λ-values estimated from data points at 2–8 hours (I), 2–12 hours (II), 2–24 hours (III), 3–12 hours (IV), 3–24 hours (V), 4–24 hours (VI), 6 hours (VII) and 6–24 hours (VIII)

$F_{rel,inf}$ was calculated as $F_{rel} = AUC_{0-inf}^{test} \cdot Dose^{ref} / AUC_{0-inf}^{ref} \cdot Dose^{test}$ $F_{rel,t}$ was calculated as $F_{rel} = AUC_{0-t}^{test} \cdot Dose^{ref} / AUC_{0-t}^{ref} \cdot Dose^{test}$ Mean values for the relative bioavailability (relative to cyclodextrin solution) were almost identical irrespective of the calculation being made with respect to the serum concentration time curve to infinity ($AUC_{0-inf}$) or to the last measurable concentration ($AUC_{0-t}$). Mean values for the latter AUC parameter were 997 nmol·h·$L^{-1}$ (reference formulation), 1066 nmol·h·$L^{-1}$ (Akosoft 3103), 848 nmol·h·$L^{-1}$ (Tween 80/Kollidon VA64), 700 nmol·h·$L^{-1}$ (HPC) 440 nmol.h.$L^{-1}$ (model drug substance/SLS 1:1) and 241 nmol.h.$L^{-1}$ (model drug substance/SLS 2:1). The low values for the two SLS formulations are in line with the low $C_{max}$ values observed for these formulations.

The corresponding mean relative bioavailability-values were 1.10 (Akosoft 3103), 0.89 (Tween 80/Kollidon VA64), 0.77 (HPC), 0.46 (model drug substance/SLS 1:1) and 0.29 (model drug substance/SLS 2:1).

The low relative bioavailability observed for the two SLS-formulations was not expected as a similar formulation, albeit with a model drug substance/SLS-ratio at 2:1, administered in a previous study resulted in a mean relative bioavailability of 1.20. Apparently there is a critical concentration below which the dissolution- and absorption enhancing properties of SLS are limited.

All formulations administered to animal F 1039 resulted in a relative bioavailability (based on $AUC_{0-inf}$) around or above unity (range 0.98–1.53). The relative bioavailability determined in this dog for the different formulations therefore contributes considerably to the mean $F_{rel}$. This is especially the case for the two SLS formulations where the relative bioavailability is very low for the other three dogs. When this dog was excluded mean values of 0.24 and 0.06 were found for model drug substance/SLS-ratios of 1:1 and 2:1, respectively.

The mean apparent half life determined after administration of the various treatments were 4.5 hours (HPC suspension), 4.8 hours (5% Captisol® and model drug substance/SLS 2:1), 4.9 hours (Akosoft 3103), 5.2 hours (model drug substance/SLS 1:1) and 6.4 hours (Tween 80/Kollidon VA64). Mean oral clearances (CL/F) were comparable for treatments with HPC (7.01 L·$kg^{-1}$·$h^{-1}$), 5% Captisol® (5.04 L·$kg^{-1}$·$h^{-1}$), Tween 80/Kollidon VA64 (5.54 L·$kg^{-1}$·$h^{-1}$) and Akosoft 3103 (4.70 L·$kg^{-1}$·$h^{-1}$). As a consequence of the low $AUC_{0-inf}$ values the two treatments with SLS show relatively high CL/F values at 12 L·$k^{-1}$·$h^{-1}$ (model drug substance/SLS 1:1) and 50 L·$^{-1}$·$h^{-1}$ (model drug substance/SLS 2:1).

Mean volumes of distribution ($V_z$/F) observed were 29.6 L·$k^{-1}$ (HPC), 32.7 L·$k^{-1}$ (Akosoft 3103), 34.9 L·$^{-1}$ (5% Captsol®) and 52.5 L·$^{-1}$ (Tween 80/Kollidon VA64). Again the values for the two SLS formulations were relatively higher at 158 L·$k^{-1}$ and 352 L·$k^{-1}$.

Pharmacokinetic parameters estimated for the reference solution were consistent with values found in a previous formulation study performed on identical animals.

As supplement to these data other formulations have been prepared including Captisol formulations: B (similar to the one in the previous study), and three formulations prepared according to the invention, formulation G, H and I. These formulations include mixtures of glycerides. Formulations G, H and I (granulate in capsule) have been manufactured by melt spraying.

Preparation of Test Formulation G, H and I According to the Invention

Preparation of a Particulate Material—Melt-spraying Process

Starting Materials

Kimol C 8–50 (Mono-diglycerid on medium chain fatty acids) (Cognis)

Viscoleo (medium chain triglycerides) (Grünau Illertissen)

Rylo MG 18 Pharma (Danisco Cultor)

Sodium lauryl sulfate (Millchem Limited)

Ascorbyl palmitate (Merck)

Model drug substance (the same substance is used throughout Example 5)

Lactose 350 M (DMV)

Equipment

Fluid bed Strea-1 (Aeromatic-Fielder)

Compositions

| Material | Formulation G g | Formulation H g | Formulation I g |
|---|---|---|---|
| Rylo MG 18 | 25.8 | 25.8 | 25.8 |
| Viscoleo | 21.2 | 21.2 | 21.2 |
| Kimol | 21.2 | 21.2 | 21.2 |
| Model drug | 50.2 | 50.2 | 25.1 |
| Lactose 350 M | 202.1 | 248.1 | 275.7 |
| SLS | 46.0 | — | — |
| Ascorbyl palmitate | 1.8 | 1.8 | 1.8 |

Process Conditions

The process conditions are similar for the formulation G, H and I. Rylo MG 18 was melted by heating to 70° C. in a pressure tank and the liquids Viscoleo and Kimol were added. The melt was pumped through a heated tube (80° C.) to the binary nose in the fluid bed at a tank pressure of 0.2 Bar. The atomizing air was heated to 140° C. The inlet air temperature of the fluid bed was 22° C.

The melt was sprayed on fluidized material consisting of the particulate materials, which include the model drug substance, lactose and ascorbyl palmitate and for formulation G; sodium lauryl sulfate. The flow rate was 20–30 g/min. The maximum product temperature was 32° C. at the end of the process.

Product Characteristic

Granular product with a particle size under 0.7 mm.

The product was filled into capsules (250 mg corresponding to 30 mg base for Formulation G and H). 500 mg corresponding to 30 mg base for formulation I.

Example 6

Proof of Concept Based on Data From Development Project with Nifedipine

Nifedipine is a yellow crystalline substance, practically insoluble in water with a solubility of <56 mg/L at 25° C. It has a molecular weight of 346.3 and a melting range between 172–174° C. The calculated log P is 2.5 and the experimental measured value is 2.2. Nifedipine is rapidly and fully absorbed after oral administration of the marketed products, however an immediate release capsule only produce a bioavailability between 30 and 60%.

Proof of concept is based on a comparison of bioavailability of different oral formulations with a solution of the drug substance as reference, in dogs in a cross over design. A summary is given below including detailed information on the melt spraying process and tabletting (Treatment B and C)

Treatment A

Solution of nifedipine in PEG 400

| Composition | |
|---|---|
| Nifedipine | 2% w/w |
| PEG 400 | 98% w/w |

1 ml per capsule (corresponds to 20 mg nifedipine)

Treatment B

Plain tablet 20 mg Adalat® Bayer

Treatment C

Tablets prepared from a particulate material produced according to the present invention by melt spraying. Nifedipine is contemplated to be present in PEG/poloxamer as a solid solution.

Melt-spraying Process

Starting Materials

Polyethyleneglycol 6000 (Hoechst)

Poloxamer 188 (BASF)

Nifedipine (Sigma-Aldrich)

Lactose 200 mesh (DMV)

Equipment

Fluid bed Strea-1 (Aeromatic-Fielder)

Process Conditions 264.6 g PEG 6000 and 113.4 g Poloxamer 188 (70:30 w/w) were melted by heating to 90° C. in a pressure tank. 15.27 g drug substance was dissolved in the melted carriers. The melt was pumped through a heated tube (85° C.) to the binary nozzle in the fluid bed at a tank pressure of 1.6 Bar. The atomizing air was heated to 140° C. The inlet air temperature of the fluid bed was 22° C.

308 g of melt was sprayed on 300 g fluidized lactose at a flow rate of 17 g/min. The total yield was 608 g granulate. The maximum product temperature was 37° C. at the end of the process.

Product Characteristic

Granular, free flowing product with a particle size under 0.7 mm

| Tablet composition | |
|---|---|
| Nifedipine | 1.94% w/w |
| PEG 6000 | 33.71% w/w |
| Poloxamer 188 | 14.45% w/w |
| Avicel PH101 | 48.90% w/w |
| Magnesium stearate | 1.00% w/w |

Magnesium stearate was blended with the granulate for 0.5 minutes in a Turbula-mixer.

Tabletting and Tablet Characteristics

The tabletting was performed on a single punch tabletting machine Korsch EK0

Tablet shape 8 mm compound shape
Weight: 260 mg
Strength 5 mg
Mean tablet hardness (n=10) determined on a Schleuniger model 6D was 97 N
Mean disintegration time was 11.3 minutes (Ph.Eur)
Weight variation (n=20) corresponded to RSD of 1.15%
Dosing 4 tablets (20 mg) in a capsule Dosing One dog was dosed with the 3 different formulations A, B and C with 3 days between dosing. 2 ml of blood samples were taken at pre-dose and 0.25, 0.5, 1, 1.5, 2, 4, 8 and 24 hours after administration. The analysis of nifedipine was performed on respective plasma samples.

Pharmacokinetic Results

The pharmacokinetic data are shown in the Table below

| Formulation | A | B | C |
|---|---|---|---|
| $T_{max}$ (h) | 0.5 | 0.5 | 1.0 |
| $C_{max}$ (ng/ml) | 66.6 | 22.0 | 61.0 |
| $AUC_{0-inf}{}^a$ (ng h/ml) | 172.2 | 22.2 | 53.1 |
| $F_{rel}{}^b$ (%) | 100 | 12.9 | 30.8 |

Calculated as
$^a AUC_{last} + C_{last}/\lambda_z$;
$^b AUC_{0-inf,po} * D_{ref}/(AUC_{0-inf,ref} * D_{po})$ The bioavailability $F_{rel}$ is calculated relative to formulation A, representing a solution of nifedipine in PEG 400. The corresponding plasma profiles are shown in FIG. 7.

Conclusion

Apparently the solid solution of nifedipine in PEG6000/Poloxamer (formulation C) results in significant higher bioavailability compared to a plain tablet formulation (Adalat).

Example 7

Neusilin as Absorption Material in Controlled Agglomeration

Background

It is established that magnesium aluminium silicate (Carrisorb, Gelsorp, Magnabite) is suitable in absorption of liquids and commonly used as a viscosity increasing, a tablet disintegrant and a tablet binding agent.

Neusilin (Fuji Chemical Industries) is a magnesium aluminometasilicate based on a polymeric reaction of sodium silicate having a siloxane structure (U.S. Pat. No. 3,959,444) in combination with a mixture or sodium aluminate and magnesium salts.

Neusilin US2 is a spray dried free flowing material with a particle size of approx. 80 μm and a specific surface area of 300 m²/g.

Two experiments (A and B) have been performed where PEG 6000 is sprayed on fluidized Neusilin in a fluid bed Strea-1.

Experiment A is performed under conditions of controlled agglomeration keeping the temperature difference over 10° C. between the product and the melting point of PEG 6000 (59° C.).

Experiment B is performed under heating condition of the inlet air (50–70° C.) resulting in a product temperature under the 10° C. temperature difference.

Experiment A

Equipment
Fluid bed Strea-1 (Aeromatic-Fielder)

Process Conditions 1000 g PEG 6000 was melted by heating to 90° C. in a pressure tank. The melt was pumped through a heated tube (85° C.) to the binary nozzle in the fluid bed at a tank pressure of 1.5 Bar. The atomizing air was heated to 140° C. The inlet air temperature of the fluid bed was 22° C.

584 g of melt was sprayed on 150 g fluidized Neusilin US2 at a flow rate of 19 g/min. The total yield was 734 g granulate. The maximum product temperature was 45° C. at the end of the process. The concentration of PEG 6000 in the particulate material obtained was 79.6% w/w.

Product Characteristic

Granular, free flowing product with a particle size $d_{gw}$ of 409 μm.

| Tablet composition | |
|---|---|
| PEG 6000 | 79.6% |
| Neusilin | 20.4% |

Tabletting and Tablet Characteristics

The tabletting was performed on a single punch tabletting machine Korsch EK0. It was not necessary to add further excipients for the tabletting procedure.

Tablet shape 8 mm compound cup
Weight: 200 mg
Mean tablet hardness (n=10) determined on a Schleuniger model 6D was 48.6 N
Mean disintegration time was 22.4 minutes (Ph.Eur)
Weight variation (n=20) corresponded to RSD of 0.6%

Experiment B

Equipment
Fluid bed Strea-1 (Aeromatic-Fielder)

Process Conditions 800 g PEG 6000 was melted by heating to 90° C. in a pressure tank. The melt was pumped through a heated tube (85° C.) to the binary nozzle in the fluid bed at a tank pressure of 1.5 Bar. The atomizing air was heated to 140° C. The inlet air temperature of the fluid bed was 60° C.

505 g of melt was sprayed on 150 g fluidized Neusilin US2 at a flow rate of 19 g/min. The total yield was 655 g granulate. The maximum product temperature was 58° C. at the end of the process.

Product Characteristic

Granular, free flowing product with a particle size under 0.7 mm.

| Tablet composition | |
|---|---|
| PEG 6000 | 77.1% |
| Neusilin | 22.9% |

Tabletting and Tablet Characteristics

Tabletting was not possible due to adhesion to the punches.

Conclusion

Neusilin US2 acts as an absorption agent for the melted carrier sprayed on the fluidized material.

Surprisingly high amount of carrier was applicable corresponding to a total amount of carrier exceeding 80% without getting uncontrolled agglomeration. In Experiment A, the temperature difference between product and melting point of the carrier exceeded 10° C. Further, direct tabletting of the product without adding lubricant was successfully performed.

Increasing the inlet temperature of the fluidized bed (Experiment B) exceeding the temperature limits for controlled agglomeration (recognized for the traditionally employed excipients) did not result in uncontrolled agglomeration as expected. This is most likely due to the high absorption capacity of Neusilin preventing free surface liquid to form bondings between the fluidized particles. However, uncontrolled agglomeration occurred at the end of the process (77.1% PEG 6000). Direct compression of the product was not possible due to adhesion to the punches indicating surface free PEG in the agglomerates, which might be due to the elevated product temperature in the agglomeration process.

To sum up, it is possible to obtain controlled agglomeration even in those cases where no or only a small temperature difference is present between the carrier and the second composition. This applies especially for substances like Neusilin and the like.

Example 8

Lubricant Effect of Neusilin in Comparison with Magnesium Stearate and Aerosil 200

A sticky granulate was produced by controlled agglomeration. PEG 1500 (melting range of from about 44 to about 48° C.) was applied on lactose 200 mesh in a fluid bed Strea-1. The composition of the product was as follows:

| | |
|---|---|
| Lactose 200 mesh | 300 g |
| PEG 1500 | 200 g |

The granulate was sieved through a 0.71 mm mesh size.

A part of the granulate was blended with the different substances for 3 minutes in a Turbula mixer in order to determine any lubricating effect. Two of the substances used, namely magnesium stearate and Aerosil, are known lubricants. The substances employed were:

Neusilin ULF2 (Fuji Chemical Industries)

Magnesium stearate (Magnesia GmbH)

Aerosil 200 (colloidal silicon dioxide), (Degussa AG)

Tablets were produced on a single punch tabletting machine Korsch EK0, instrumented with force transducer on the filling device measuring the force to push off the tablet from the lower punch.

Tablet diameter 8 mm. Tablet shape: Compound cup

Tablet weight: 200 mg

The results are summarised in the Table below

| Lubricant | Conc. % | Adhesion to tablet punches | Mean Push off force N |
|---|---|---|---|
| Neusilin | 2 | no | 4.5 |
| | 4 | no | 1.1 |
| Mg-stearate | 1 | Adhesion | n.m. |
| Aerosil 200 | 0.5 | Adhesion | n.m |
| | 1 | Adhesion | n.m |

Conclusion

Neusilin and Aerosil provided excellent flowability to the sticky granular product, whereas magnesium stearate did not have this effect. Aerosil is normally used as lubricant in the concentrations below 0.5% and is primarily used to improve the flowability of cohesive materials.

The anti-adhesive property of Neusilin is superior to both magnesium stearate and Aerosil. Granules blended with either 2 or 4% of Neusilin was compressed without any adhesion to the punches. As shown in the Table the adhesion to the lower punch was significantly decreased when increasing the concentration of Neusilin from 2 to 4%. The push off force was not monitored (n.m.) for the other lubricants since compression of tablets was not possible due to immediately adhesion to the punches.

Thus, the results demonstrate that Neusilin is an excellent lubricant having anti-adhesive properties.

The invention claimed is:

1. A method for preparing particulate material, comprising:

i) spraying a first composition on a second composition, wherein the first composition comprises one or more therapeutically or prophylactically active substances and a carrier in liquid form, wherein the carrier has a melting point of at least about 5° C., and the second composition comprises a material in solid form at a temperature corresponding to or below the melting point of the first composition, and ii) agglomerating the first composition with the second composition to obtain the particulate material, wherein the therapeutically or prophylactically active substance has an aqueous solubility of at most about 3 mg/ml at 25° C. and a pH of about 7.4 and wherein the particulate material obtained comprises a geometric weight mean diameter from between about 75 to about 2000 μm.

2. The method of claim 1, wherein the therapeutically active or prophylactic substance has an aqueous solubility of at most about 1 mg/ml at about 25° C. and a pH of about 7.4.

3. The method of claim 1, wherein the therapeutically or prophylactically active substance has an aqueous solubility of at most about 0.01 mg/ml at about 25° C. and a pH of about 7.4.

4. The method of claim 1, wherein the carrier has a melting point of about 10° C. or more.

5. The method of claim 1, wherein the carrier has a melting point of at least about 20° C.

6. The method of claim 1, wherein the carrier has a melting point of at least about 25° C.

7. The method of claim 1, wherein the temperature of the second composition is at least about 2° C. below the melting point temperature of the carrier or the first composition.

8. The method of claim 1, wherein the temperature of the second composition is at least about 5° C. below the melting point temperature of the carrier or the first composition.

9. The method of claim 1, wherein the temperature of the second composition is at least about 10° C. below the melting point temperature of the carrier or the first composition.

10. The method of claim 1, which agglomeration is carried out in a high shear mixer, a low shear mixer, or a fluid bed.

11. The method of claim 1, which agglomeration is carried out in a fluid bed and wherein the first composition is sprayed on the second composition in a fluidized state.

12. The method of claim 1, wherein the spraying is performed through a spraying device equipped with temperature controlling means.

13. The method of claim 1, wherein the particulate material has a geometric weight mean diameter $d_{gw}$ of at least about 10 micrometer.

14. The method of claim 1, wherein the particulate material has a geometric weight mean diameter $d_{gw}$ of between about 20 micrometer and about 2000 micrometer.

15. The method of claim 1, wherein the concentration of the carrier in the particles is from about 5 to about 95% v/v.

16. The method of claim 1, wherein the first composition is liquefied by heating the carrier or the first composition to a temperature, which causes the carrier or the carrier composition to melt.

17. The method of claim 16, wherein the liquefied carrier or carrier composition has a viscosity (Brookfield DV-III) of at most about 800 mPas at a temperature of at most about 100° C.

18. The method of claim 1, wherein the first composition is essentially non-aqueous and contains at most about 20% w/w water.

19. The method of claim 1, wherein the carrier has a melting point of at most about 300° C.

20. The method of claim 1, wherein the carrier is a hydrophilic carrier, a hydrophobic carrier, a surfactant or a mixture thereof.

21. The method of claim 20, wherein the carrier is selected from one or more of polyether glycols; polyoxyethylenes, polyoxypropylenes; poloxamers and mixtures thereof.

22. The method of claim 20, wherein the carrier is selected from one or more of polyethylene glycol and polypropylene glycol.

23. The method of claim 20, wherein the carrier is selected from one or more of xylitol, sorbitol, potassium sodium tartrate, sucrose tribehenate, glucose, rhamnose, lactitol, behenic acid, hydroquinon monomethyl ether, sodium acetate, ethyl fumarate, myristic acid, citric acid; polyglycolized glycerides Gelucire 50/13, Gelucire 44114, Gelucire 50/10, Gelucire 62/05; Sucro-ester 7, Sucro-ester 11, Sucro-ester 15, maltose, mannitol and mixtures thereof.

24. The method of claim 20, wherein the carrier is selected from one or more of straight chain saturated hydrocarbons, sorbitan esters paraffins; fats and oils, cacao butter, beef tallow, lard, polyether glycol esters; higher fatty acids, stearic acid, myristic acid, palmitic acid, higher alcohols, cetanol, stearyl alcohol, low melting point waxes, glyceryl monostearate, hydrogenated tallow, myristyl alcohol, stearyl alcohol, substituted and/or unsubstituted monoglycerides, substituted and/or unsubstituted diglycerides, substituted and/or unsubstituted triglycerides, yellow beeswax, white beeswax, camauba wax, castor wax, japan wax, acetylate monoglycerides; NVP polymers, PVP polymers, and acrylic polymers.

25. The method of claim 1, wherein the carrier is polyethylene glycol having an average molecular weight from between about 400 to about 35,000.

26. The method of claim 1, wherein the carrier is selected from the group consisting of polyethylene glycol 1,000, polyethylene glycol 2,000, polyethylene glycol 3,000, polyethylene glycol 4,000, polyethylene glycol 5,000, polyethylene glycol 6,000, polyethylene glycol 7,000, polyethylene glycol 8,000, polyethylene glycol 9,000 polyethylene glycol 10,000, polyethylene glycol 15,000, polyethylene glycol 20,000, and polyethylene glycol 35,000.

27. The method of claim 1, wherein the carrier is polyethylene oxide having a molecular weight of from between about 2,000 to about 7,000,000.

28. The method of claim 1, wherein the carrier is a poloxamer.

29. The method of claim 1, wherein the carrier is selected from the group, consisting of Poloxamer 188, Poloxamer 237, Poloxamer 338 and Poloxamer 407.

30. The method of claim 1, wherein the carrier is selected from the group consisting of sorbitan esters, sorbitan. diisostearate, sorbitan dioleate, sorbitan monolaurate, sorbitan monoisostearate, sorbitan monooleate, sorbitan monopalmitate, sorbitan monostearate, sorbitan sesqui-isostearate, sorbitan sesquloleate, sorbitan sesquistearate, sorbitan tri-isostearate, sorbitan trioleate, sorbitan tristearate and mixtures thereof.

31. The method of claim 1, wherein the first composition comprises a mixture of one or more of hydrophilic and hydrophobic carriers.

32. The method of claim 1, wherein the second composition comprises one or more therapeutically active or prophylactic substances.

33. The method of claim 1, wherein the first composition further comprises one or more pharmaceutically acceptable excipients.

34. The method of claim 33, wherein the pharmaceutically acceptable excipient is selected from the group consisting of fillers, binders, disintegrants, glidants, coloring agents, taste-masking agents, pH-adjusting agents, solubilizing agents, stabilizsing agents, wetting agents, surface active agents, and antioxidants.

35. The method of claim 1, wherein the second composition comprises one or more pharmaceutically acceptable excipients.

36. The method of claim 35, wherein the pharmaceutically acceptable excipient is one or more of fillers, binders, disintegrants, glidants, coloring agents, taste-masking agents, pH-adjusting agents, solubilizing agents, stabilizing agents, wetting agents, surface active agents, and antioxidants.

37. The method of claim 1, wherein the first or the second composition comprises a cosmetically active substance, a beneficial substance, a food substance, or a nutrient substance.

38. The method of claim 1, wherein the second composition comprises magnesium aluminosilicate or magnesium aluminometasilicate and the amount of carrier in the particulate material is at least about 30% v/v.

39. The method of claim 38, wherein the amount of carrier in the particulate material is at least about 40% v/v.

40. The method of claim 38, wherein the amount of carrier in the particulate material is at least about 50% v/v.

41. The method of claim 1, wherein the particulate material is suitable for use in the preparation of pharmaceutical, cosmetic or food composition in a liquid, semi-solid or solid form.

42. The method of claim 1, wherein the particulate material is suitable for use in the preparation of tablets.

43. A method for improving the shelf-life of a pharmaceutical composition comprising an oxidation-sensitive therapeutically or prophylactically active substance, comprising subjecting the substance, before or during manufacture of the pharmaceutical composition, to the method of claim 1 by incorporating the substance in the first composition.

44. A method for preparing particulate material comprising spraying, on a second composition in a fluidized state, an amount of a first composition effective for agglomerating the second composition to obtain the particulate material, wherein the first composition comprises one or more therapeutically or prophylactically active substances having an aqueous solubility of at most about 3 mg/ml at 25° C. and a pH of about 7.4 and a carrier in liquid form, wherein the carrier has a melting point of at least about 5° C., the second composition comprises a material in solid form at a temperature corresponding to or below the melting point of the first composition, and the particulate material obtained has a geometric weight mean diameter from between about 75 to about 2000 μm.

* * * * *